US009696266B2

(12) United States Patent
Suyama

(10) Patent No.: US 9,696,266 B2
(45) Date of Patent: Jul. 4, 2017

(54) NONDESTRUCTIVE INSPECTION DEVICE AND METHOD FOR CORRECTING LUMINANCE DATA WITH NONDESTRUCTIVE INSPECTION DEVICE

(75) Inventor: Toshiyasu Suyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 657 days.

(21) Appl. No.: 14/356,480

(22) PCT Filed: Aug. 22, 2012

(86) PCT No.: PCT/JP2012/071192
§ 371 (c)(1),
(2), (4) Date: May 22, 2014

(87) PCT Pub. No.: WO2013/069354
PCT Pub. Date: May 16, 2013

(65) Prior Publication Data
US 2014/0294151 A1    Oct. 2, 2014

(30) Foreign Application Priority Data

Nov. 8, 2011 (JP) ................. 2011-244682

(51) Int. Cl.
*G01N 23/083* (2006.01)
*G01N 23/04* (2006.01)
*G01V 5/00* (2006.01)

(52) U.S. Cl.
CPC ......... *G01N 23/043* (2013.01); *G01N 23/083* (2013.01); *G01V 5/0041* (2013.01); *G01N 2223/423* (2013.01); *G01N 2223/618* (2013.01); *G01N 2223/643* (2013.01)

(58) Field of Classification Search
CPC ....... G01N 2223/423; G01N 2223/618; G01N 2223/643; G01N 23/043; G01N 23/083; G01V 5/0041
See application file for complete search history.

(56) References Cited

U.S. PATENT DOCUMENTS

| 4,641,352 A * | 2/1987 | Fenster | ................... G06T 5/006 |
| | | | 382/130 |
| 4,685,146 A * | 8/1987 | Fenster | ................... G06T 5/006 |
| | | | 382/282 |
| 5,825,032 A * | 10/1998 | Nonaka | ................... H04N 5/325 |
| | | | 250/370.09 |

(Continued)

FOREIGN PATENT DOCUMENTS

| CN | 101836867 | 9/2010 |
| EP | 0785674 | 7/1997 |

(Continued)

OTHER PUBLICATIONS

Ilsever et al., Two-dimensional Change Detection Methods: Remote Sensing Applications, 2012, ISBN 978-1-4471-4254-6, Chapter 2.*

(Continued)

*Primary Examiner* — David J Makiya
*Assistant Examiner* — John Corbett
(74) *Attorney, Agent, or Firm* — Drinker Biddle & Reath LLP

(57) ABSTRACT

A nondestructive inspection device 1 comprises an X-ray indicator 20, a low-energy detector 32, a high-energy detector 42, a low-energy transmittance calculation unit 72, a high-energy transmittance calculation unit 74, a detection unit 76, and a correction unit 78. The calculation unit 72 calculates a value indicating the transmittance of transmission X-rays in a low energy range. The calculation unit 74 calculates a value indicating the transmittance of transmission X-rays in a high energy range. The detection unit 76 detects a positional deviation detail of the X-ray indicator 20 according to a ratio between the transmittances calculated by both of the calculation units 72, 74. When the positional deviation detail of the X-ray indicator 20 is detected by the detection unit 76, according to the positional deviation detail, the correction unit 78 corrects X-ray luminance data detected by the detectors 32, 42.

11 Claims, 15 Drawing Sheets

(56) References Cited

U.S. PATENT DOCUMENTS

| | | | | |
|---|---|---|---|---|
| 5,841,832 A | * | 11/1998 | Mazess | A61B 6/032 250/367 |
| 2002/0027201 A1 | * | 3/2002 | Agano | G01V 5/0041 250/370.11 |
| 2002/0181652 A1 | * | 12/2002 | Ohtsuki | G01N 23/04 378/57 |
| 2006/0171504 A1 | | 8/2006 | Sommer et al. | |

FOREIGN PATENT DOCUMENTS

| | | |
|---|---|---|
| JP | H3-109679 | 5/1991 |
| JP | H04-2907 A | 1/1992 |
| JP | 2000-121579 A | 4/2000 |
| JP | 2000-298198 A | 10/2000 |
| JP | 2001-133554 A | 5/2001 |
| JP | 2010-091483 A | 4/2010 |
| JP | 2011-015732 A | 1/2011 |
| JP | 2012-073056 A | 4/2012 |
| JP | 2012-194101 A | 10/2012 |
| WO | WO 01/29557 | 4/2001 |
| WO | WO-2010/055728 A1 | 5/2010 |
| WO | WO 2010/095530 | 8/2010 |
| WO | WO-2011/033837 A1 | 3/2011 |
| WO | WO-2011/033838 A1 | 3/2011 |

OTHER PUBLICATIONS

English-language translation of International Preliminary Report on Patentability (IPRP) dated May 22, 2014 that issued in WO Patent Application No. PCT/JP2012/071192.

\* cited by examiner

Fig.3
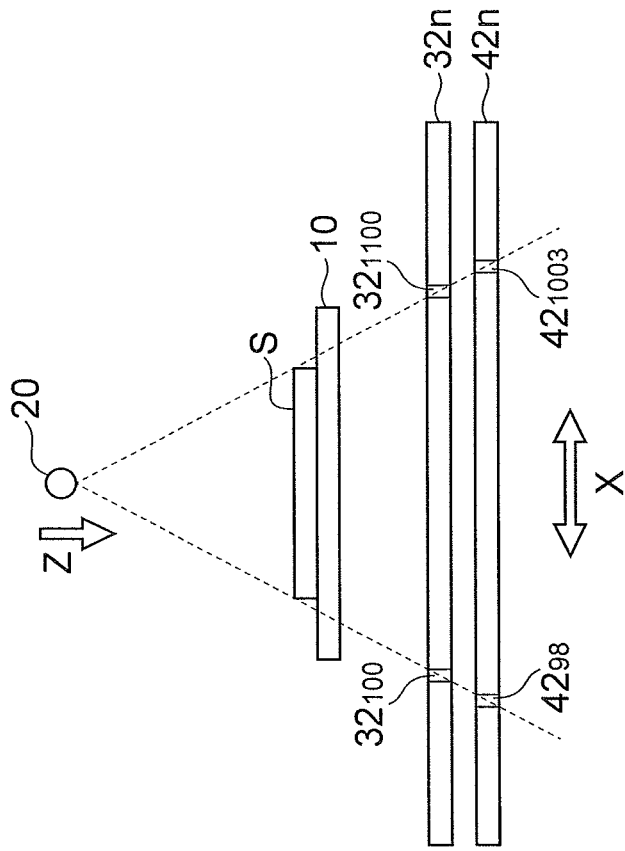
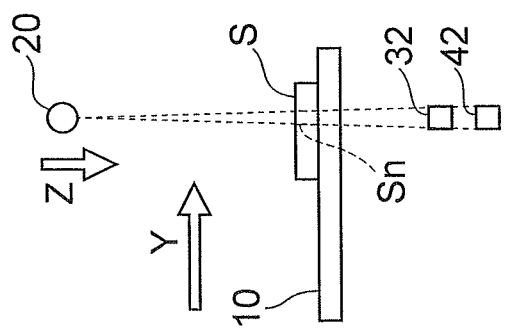

*Fig.4*
(a)
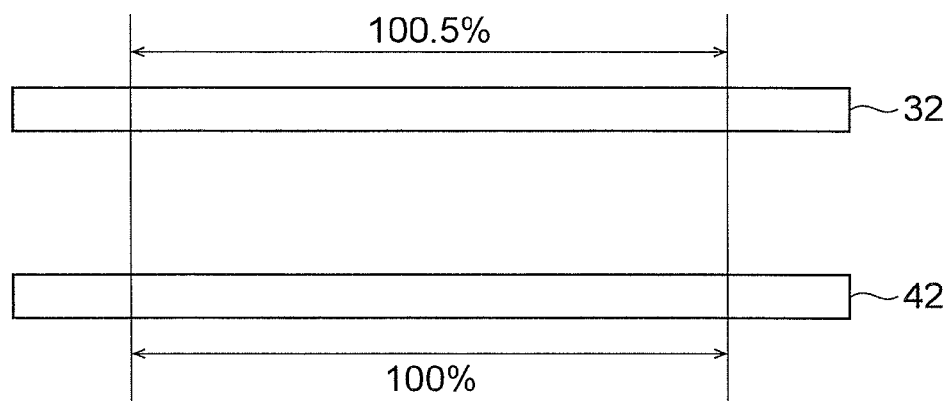
(b)
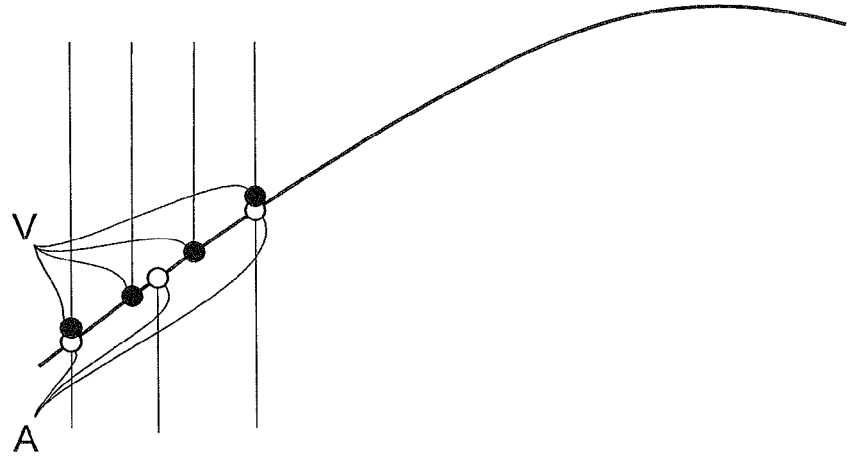

Fig.8
(a)
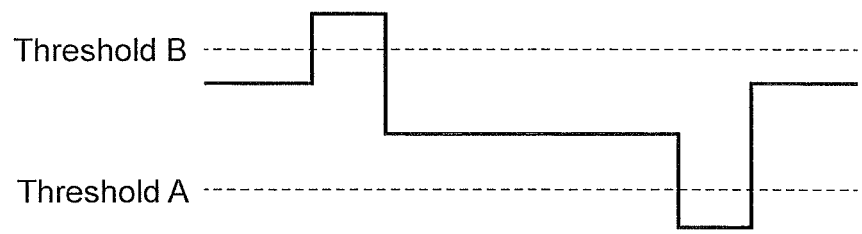
(b)
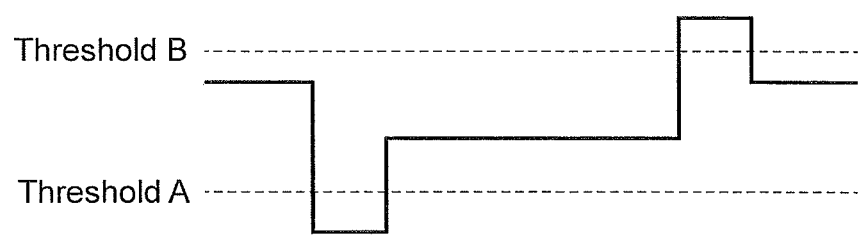
(c)
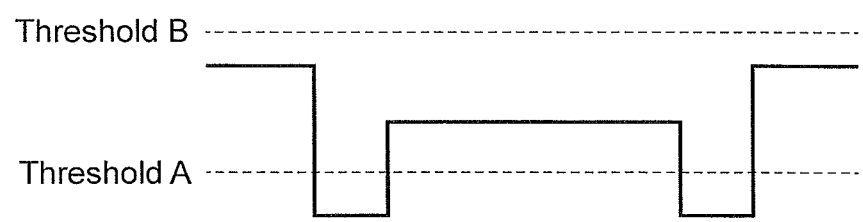
(d)
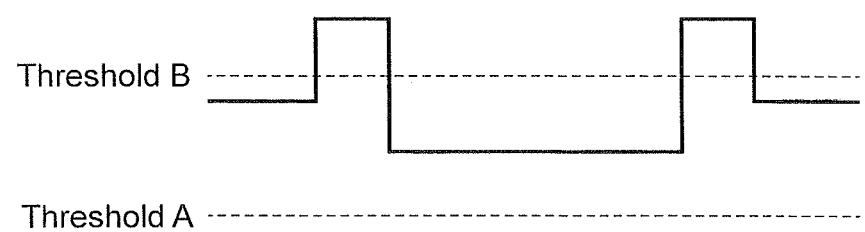

Fig. 11
(b)
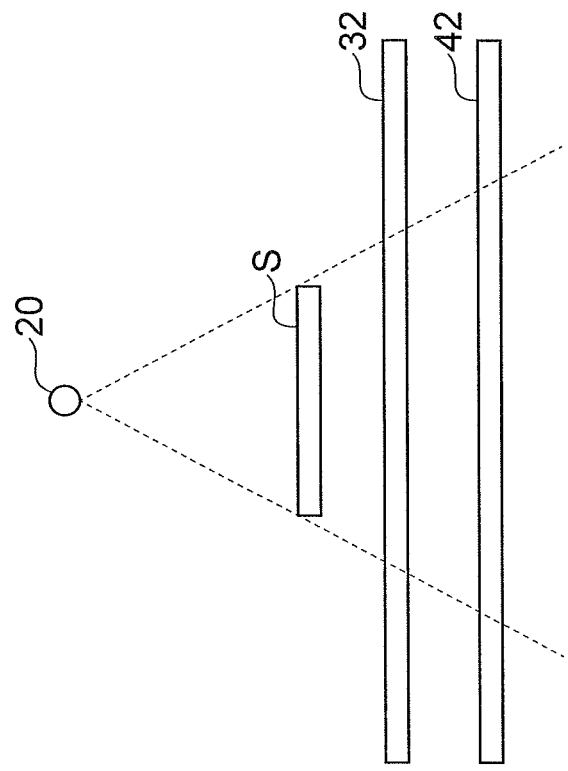
(a)
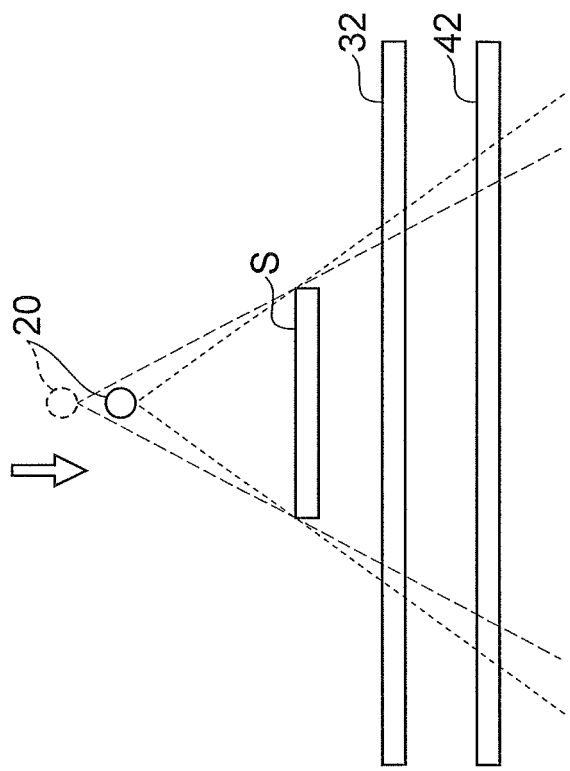

NONDESTRUCTIVE INSPECTION DEVICE AND METHOD FOR CORRECTING LUMINANCE DATA WITH NONDESTRUCTIVE INSPECTION DEVICE

TECHNICAL FIELD

The present invention relates to a nondestructive inspection device and a method for correcting luminance data with the nondestructive inspection device.

BACKGROUND ART

Inspection devices of a dual energy type have been known which irradiate subjects to be inspected such as foods and industrial products with radiations such as X-rays and detect the radiations transmitted through the subjects in different ranges such as low and high energy ranges, so as to perform nondestructive inspections. Such a nondestructive inspection device can acquire radiation images in low and high energy ranges at the same time.

Carrying out predetermined operations (such as division, subtraction, addition, and multiplication) between the radiation images acquired in the different energy ranges makes it possible to highly accurately determine distributions of components intricately mixing together, detect foreign matters which are hard to get a contrast, and so forth. For acquiring radiation images in different energy ranges, such an inspection device is equipped with detectors corresponding to the respective energy ranges and employs a structure in which the detectors are arranged in a vertical row (see FIG. 9 of Patent Literature 1), for example.

CITATION LIST

Patent Literature

Patent Literature 1: Japanese Patent Application Laid-Open No. H04-002907

SUMMARY OF INVENTION

Technical Problem

Meanwhile, in the inspection device constructed such that the detectors are stacked in two stages, its radiation source is a point light source, while there is a distance between an image pickup device included in the detector on the upstream side in an irradiation direction of the radiation and an image pickup device included in the detector on the downstream side, whereby a deviation occurs between images acquired by the respective image pickup devices (see FIG. 3(b)). Therefore, correspondences between pixels of the detectors on the upstream and downstream sides are determined beforehand by using a calibration member and the like, so that a radiation image in which the pixels of the upstream and downstream detectors correspond with each other can be acquired when performing a nondestructive inspection device.

However, when continuously performing nondestructive inspections, the light source position of the radiation source may shift (exhibit a focal shift) due to displacement or deformation (thermal expansion) caused by the temperature of the radiation source or nondestructive inspection device, whereby the pixels of the upstream and downstream detectors brought into correspondence with each other may fail to correspond with each other. If the pixels thus fail to correspond with each other between the detectors, when carrying out a predetermined operation between radiation images, pseudo-edges occurring in results of operations and the like may prevent appropriate radiation operation images from being acquired, thereby lowering the measuring accuracy in the nondestructive inspection. When continuously performing nondestructive inspections in-line, calibration is hard to perform for each inspection, which makes it necessary to detect early if the pixels fail to correspond with each other and then correct radiation images such that the pixels correspond with each other.

Solution to Problem

The nondestructive inspection device in accordance with one aspect of the present invention is a device comprising a conveyor unit, a radiation source, first and second radiation detectors, first and second calculation units, a detection unit, and a correction unit. The conveyor unit conveys a subject to be inspected in a predetermined direction. The radiation source irradiates the conveyor unit with a radiation directed so as to intersect a conveying direction caused by the conveyor unit. The first radiation detector detects the radiation emitted from the radiation source in a first energy range. The second radiation detector detects the radiation emitted from the radiation source in a second energy range higher than the first energy range.

The first calculation unit calculates from luminance data of the radiation detected by the first radiation detector a value indicating a first transmittance in the first energy range of the radiation transmitted from the radiation source through the subject. The second calculation unit calculates from luminance data of the radiation detected by the second radiation detector a value indicating a second transmittance in the second energy range of the radiation transmitted from the radiation source through the subject. According to a ratio or difference between the value indicating the first transmittance calculated by the first calculation unit and the value indicating the second transmittance calculated by the second calculation unit, the detection unit detects a positional deviation detail of the radiation source. When the positional deviation detail of the radiation source is detected by the detection unit, the correction unit corrects according to the positional deviation detail at least one of the luminance data of the radiation detected by the first and second radiation detectors.

The correction method in accordance with one aspect of the present invention is a correction method, in a nondestructive inspection device comprising a conveyor unit that conveys a subject to be inspected in a predetermined direction, a radiation source that irradiates the conveyor unit with a radiation directed so as to intersect a conveying direction caused by the conveyor unit, a first radiation detector that detects the radiation emitted from the radiation source in a first energy range, and a second radiation detector that detects the radiation emitted from the radiation source in a second energy range higher than the first energy range, for correcting at least one of luminance data detected by the first and second radiation detectors.

This correction method comprises a first calculation step, a second calculation step, a detection step, and a correction step. The first calculation step calculates from luminance data of the radiation detected by the first radiation detector a value indicating a first transmittance in the first energy range of the radiation transmitted from the radiation source through the subject. The second calculation step calculates from luminance data of the radiation detected by the second radiation detector a value indicating a second transmittance in the second energy range of the radiation transmitted from the radiation source through the subject. According to a ratio or difference between the value indicating the first transmittance calculated at the first calculation step and the value indicating the second transmittance calculated at the second calculation step, the detection step detects a positional deviation detail of the radiation source. When the positional deviation detail of the radiation source is detected by the detection step, the correction step corrects according to the positional deviation detail at least one of the luminance data of the radiation detected by the first and second radiation detectors.

In the above-mentioned aspect, the values indicating the respective transmittances in the first and second energy ranges of the radiation transmitted through the subject are calculated from luminance data, and the positional deviation detail of the radiation source is detected according to a ratio or difference between the values indicating the transmittances. While radiations such as X-rays have such a property as to be easier to pass through an object as their energy is higher, for example, referring to the values indicating transmittances of an object in both of detectors adjusted such that their pixels and the like correspond with each other can detect if and how the pixels of the detectors fail to correspond with each other, whereby the positional deviation detail can be seen. As a result, the above-mentioned aspect can detect early if the pixels of the radiation detectors fail to correspond with each other and correct luminance data from the detectors such that the pixels correspond with each other again.

The above-mentioned aspect calculates the values indicating the respective transmittances in the first and second energy ranges of the radiation by utilizing luminance data. Since the luminance data usually acquired by radiation detectors of nondestructive inspection devices are utilized, the transmittances can easily be determined without requiring new detectors to be provided separately. However, new detectors may be provided in addition. The second energy range detected by the second radiation detector is only required to be higher than the first energy range in total and may partly overlap the first energy range.

In the nondestructive inspection device and correction method in accordance with another aspect, the detection unit may store therein two thresholds of upper and lower limits set by a radiation transmittance of the subject and detect the positional deviation detail of the radiation source by comparing the ratio or difference between the values indicating the first and second transmittances with both of the upper and lower thresholds. In this case, for detecting the positional deviation detail of the radiation source, the thresholds are set according to a distinct radiation transmittance for each subject to be inspected, whereby the positional deviation detail of the radiation source can be seen more securely.

In the nondestructive inspection device and correction method in accordance with still another aspect, each of the first and second radiation detectors may have a detection region extending in a detection direction intersecting the conveying and irradiation directions, while the detection unit may detect the positional deviation detail of the radiation source by comparing with the upper and lower thresholds a transmittance pattern constituted by an assembly of ratios or differences of values indicating the first and second transmittances while corresponding to the detection region. In this case, the positional deviation detail of the radiation source can be detected by comparing the transmittance pattern with the thresholds, whereby the detection processing can be made simpler.

In the nondestructive inspection device and correction method in accordance with yet another aspect, the detection unit may determine that the radiation source is shifted in the detection direction when a location corresponding to one end of the subject in the transmittance pattern is higher than the upper threshold while a location corresponding to the other end of the subject in the transmittance pattern is lower than the lower threshold. When it is determined by the detection unit that the radiation source is shifted in the detection direction, the correction unit may perform reset processing for setting a new reference pixel by moving at least one of reference pixels for causing respective luminance data from the first and second radiation detectors to correspond with each other to another pixel, so as to correct at least one of the luminance data from the first and second radiation detectors.

When it is determined by the detection unit that the radiation source is shifted in the detection direction, the correction unit may also perform readjustment processing for readjusting a magnification of each of pixels constituting the first and second radiation detectors, so as to correct one of the luminance data from the first and second radiation detectors. This can detect a shift in the detection direction of the radiation source securely and correct the luminance data according to the shift.

In the nondestructive inspection device and correction method in accordance with a further aspect, the detection unit may determine that the radiation source is shifted in the irradiation direction if each of locations corresponding to both ends of the subject in the transmittance pattern is lower than the lower threshold or higher than the upper threshold. When it is determined by the detection unit that the radiation source is shifted in the irradiation direction, the correction unit may also perform readjustment processing for readjusting a magnification of each of pixels constituting the first and second radiation detectors, so as to correct one of the luminance data from the first and second radiation detectors.

When it is determined by the detection unit that the radiation source is shifted in the irradiation direction, the correction unit may perform reset processing for setting a new reference pixel by moving at least one of reference pixels for causing respective luminance data from the first and second radiation detectors to correspond with each other to another pixel, so as to correct at least one of the luminance data from the first and second radiation detectors. This can detect a shift in the irradiation direction of the radiation source securely and correct the luminance data according to the shift.

In the nondestructive inspection device in accordance with a still further aspect, the second radiation detector may be located downstream of the first radiation detector in the irradiation direction of the radiation. This can detect early if pixels of radiation detectors stacked in two stages fail to correspond with each other and correct luminance data from the detectors such that the pixels correspond with each other again.

Advantageous Effects of Invention

One aspect of the present invention makes it possible to detect early if pixels of radiation detectors fail to correspond with each other and correct luminance data such that the pixels correspond with each other.

BRIEF DESCRIPTION OF DRAWINGS

FIGS. 3(a) and 3(b) are side and front views, respectively, illustrating correspondences between pixels of detectors.

FIG. 4(a) is a diagram for explaining the magnification between pixels corresponding with each other, while FIG. 4(b) is a chart illustrating an example of how to create correction data.

FIGS. 8(a) to 8(d) are charts illustrating respective transmittance patterns.

FIGS. 11(a) and 11(b) are diagrams illustrating a case where the X-ray source is shifted to the lower side of an irradiation direction Z in the nondestructive inspection device depicted in FIG. 1, while representing states before and after the shift, respectively.

DESCRIPTION OF EMBODIMENTS

In the following, preferred embodiments of the present invention will be explained in detail with reference to the accompanying drawings. In the explanation, the same constituents or those having the same functions will be referred to with the same signs while omitting their overlapping descriptions.

Figure 1:
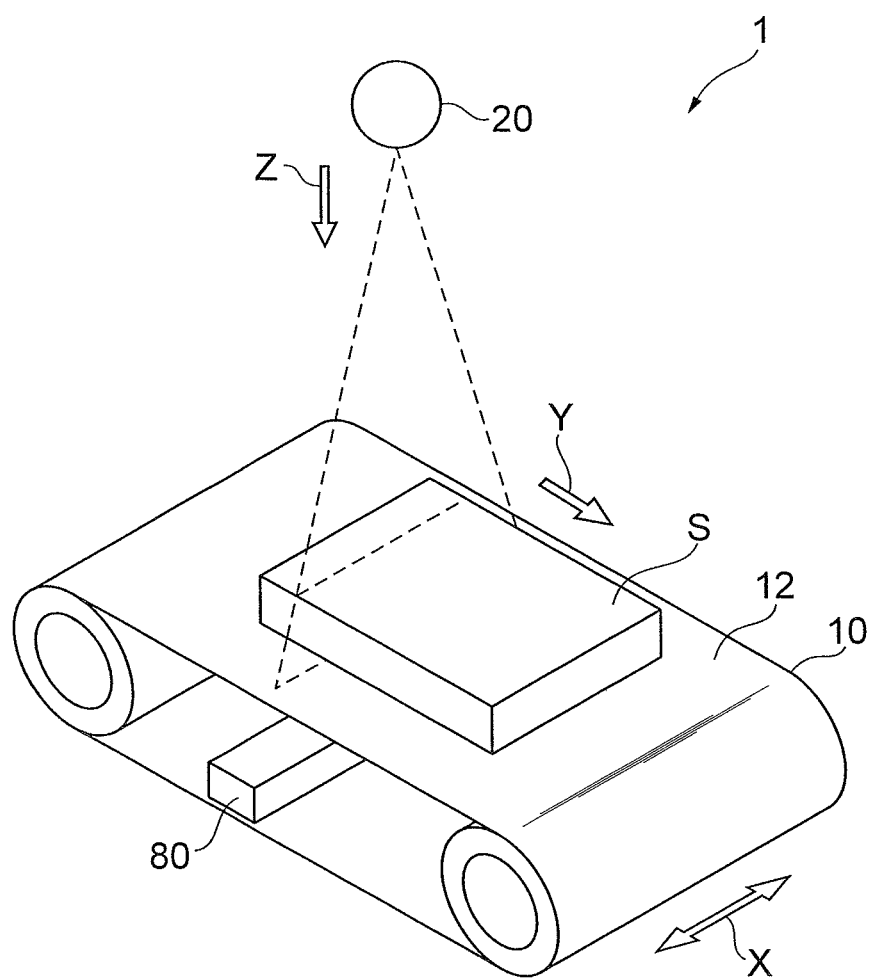
FIG. 1 is a perspective view of the nondestructive inspection device in accordance with an embodiment.
Figure 2:
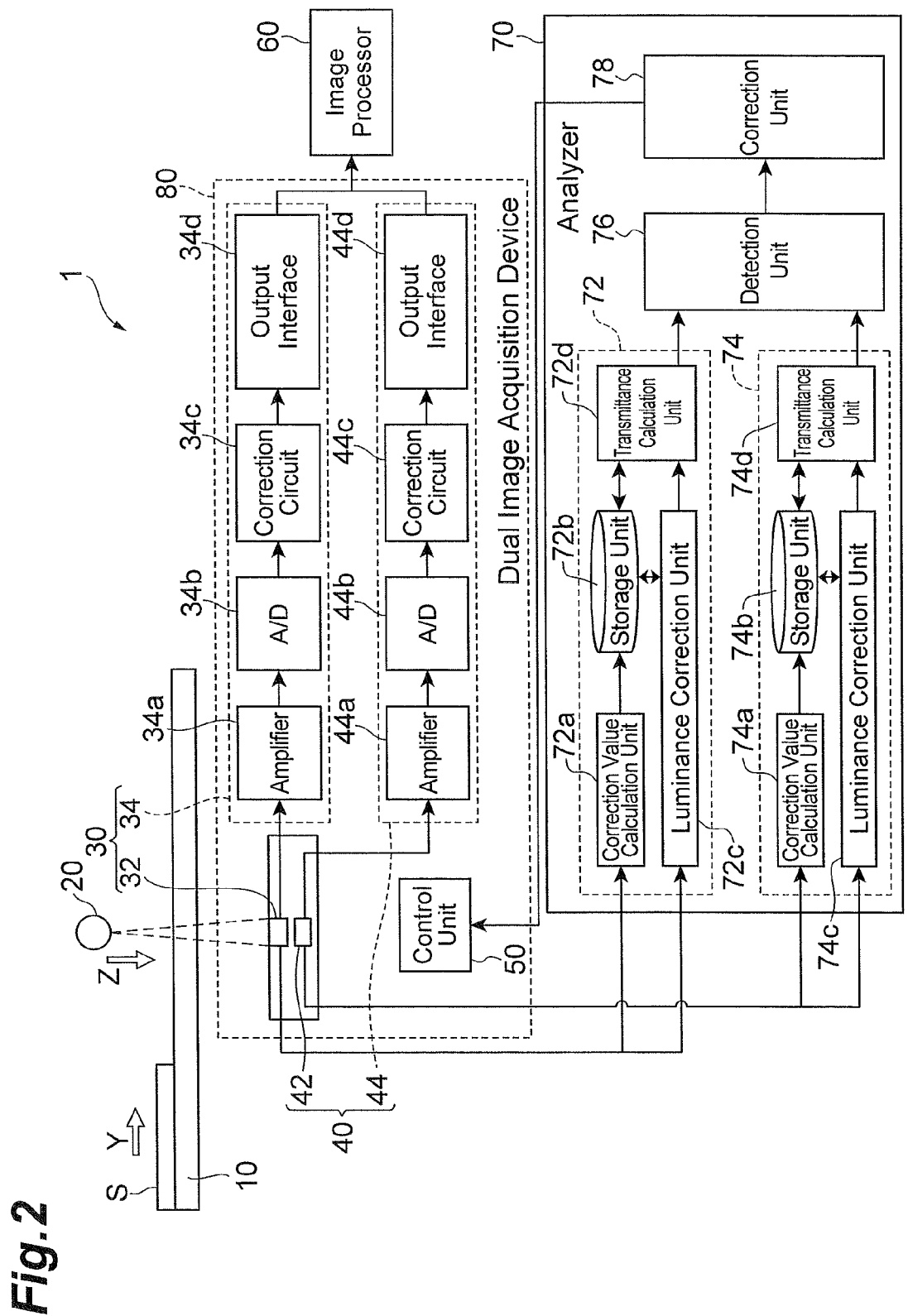
FIG. 2 is a schematic structural diagram of the nondestructive inspection device illustrated in FIG. 1.

As illustrated in FIGS. 1 and 2, a nondestructive inspection device 1 is a device which irradiates a subject S to be inspected with X-rays emitted from an X-ray source in an irradiation direction Z and detects transmission X-rays transmitted through the subject S in the emitted X-rays in a plurality of energy ranges. The nondestructive inspection device 1 inspects foreign matters in the subject S, baggage, and the like included by using a transmitted X-ray image. The nondestructive inspection device 1 comprises a belt conveyor 10, an X-ray irradiator 20, a low-energy image acquisition unit 30, a high-energy image acquisition unit 40, a control unit 50, an image processor 60, and an analyzer 70. The low-energy image acquisition unit 30, high-energy image acquisition unit 40, and control unit 50 constitute a dual image acquisition device 80.

The belt conveyor 10, as illustrated in FIG. 1, has a belt unit 12 on which the subject S is mounted. The belt conveyor 10 moves the belt unit 12 in a conveying direction Y, so as to convey the subject S in the conveying direction Y at a predetermined conveying speed. The conveying speed of the subject S is 48 m/min, for example. The belt conveyor 10 can change its conveying speed to such a rate as 24 m/min or 96 m/min, for example, as necessary. The subject S to be conveyed by the belt conveyor 10, whose examples widely cover foods such as meat and retort pouches, rubber products such as tires, baggage for security check, resin products, metal products such as wires, resource materials such as minerals, wastes for separation or resource recovery, and electronic components, is not restricted in particular.

The X-ray irradiator 20 is a device for irradiating the subject S with the X-rays in the irradiation direction Z and functions as an X-ray source. The X-ray irradiator 20 is a point light source and performs such irradiation as to disperse the X-rays over a predetermined angle range in a detection direction X which is orthogonal to the irradiation direction Z and conveying direction Y. The X-ray irradiator 20 is arranged above the belt unit 12 with a predetermined distance therefrom such that the dispersing X-rays cover the whole width (in the detection direction X) of the subject S while orienting the X-ray irradiation direction Z to the belt unit 12. The X-ray irradiator 20 is constructed such that, while a predetermined divisional range $S_n$ in the longitudinal direction of the subject S (conveying direction Y) is employed as an irradiation range (see FIG. 3(a)), the whole length of the subject S is irradiated with the X-rays as being conveyed in the conveying direction Y by the belt conveyor 10.

The low-energy image acquisition unit 30 has a low-energy detector 32 and a low-energy image correction unit 34.

The low-energy detector 32 is located on the upstream side in the X-ray entrance direction Z and detects, in the X-rays emitted from the X-ray irradiator 20, those in a low-energy range transmitted through a predetermined divisional range $S_n$ of the subject S (see FIG. 3(a)), so as to generate low-energy image data. The low-energy detector 32 can similarly detect, in the X-rays emitted from the X-ray irradiator 20, those in the low-energy range transmitted through the belt conveyor 10 without the subject S.

The low-energy detector 32 includes a low-energy scintillator layer and a low-energy line sensor. The low-energy scintillator layer extends along the detection direction X and converts an image of X-rays in the low-energy range to an optical image. The low-energy line sensor has a plurality of pixels $32_n$ (n=1 to N, where N is an integer) arranged along the detection direction X (see FIG. 3(b)) and acquires a low-energy image produced by the optical image converted by the scintillator layer. The low-energy image acquired by the line sensor is constituted by an assembly of luminance data obtained for the individual pixels $32_n$ of the line sensor.

The low-energy image correction unit 34 is constructed such as to amplify and correct the low-energy-range luminance data generated for each pixel by the low-energy detector 32 and acquire thus amplified and corrected low-energy image. The low-energy image correction unit 34 has an amplifier 34a for amplifying the low-energy-range luminance data, an A/D conversion unit 34b for A/D-converting the low-energy-range luminance data amplified by the amplifier 34a, a correction circuit 34c for performing predetermined correction processing for the luminance data converted by the A/D conversion unit 34b, and an output interface 34d for outputting the luminance data corrected by the correction circuit 34c to the outside as low-energy image data.

The high-energy image acquisition unit 40 has a high-energy detector 42 and a high-energy image correction unit 44.

The high-energy detector 42 is located downstream of the low-energy detector 32 in the X-ray entrance direction Z and detects, in the X-rays emitted from the X-ray irradiator 20, those in a high-energy range transmitted through the predetermined divisional range $S_n$ of the subject S and the low-energy detector 32, so as to generate high-energy image data. The high-energy detector 42 can similarly detect, in the X-rays emitted from the X-ray irradiator 20, those in the high-energy range transmitted through the belt conveyor 10 without the subject S. The low-energy range detected by the low-energy detector 32 and the high energy range detected by the high-energy detector 42 are not required to be clearly distinguishable from each other, but may overlap each other to some extent.

The high-energy detector 42 includes a high-energy scintillator layer and a high-energy line sensor. The high-energy scintillator layer extends along the detection direction X and converts an image of X-rays in the high-energy range to an optical image. The high-energy line sensor has a plurality of pixels $42_n$ (n=1 to N, where N is an integer) arranged along the detection direction X (see FIG. 3(b)) and acquires a high-energy image produced by the optical image converted by the scintillator layer. The high-energy image acquired by the line sensor is constituted by an assembly of luminance data obtained for the individual pixels $42_n$ of the line sensor. The low-energy detector 32 and high-energy detector 42 may be constituted by identical line sensors with different scintillator layers.

The high-energy image correction unit 44 is constructed such as to amplify and correct the high-energy-range luminance data generated for each pixel by the high-energy detector 42 and acquire thus amplified and corrected high-energy image. The high-energy image correction unit 44 has an amplifier 44a for amplifying the high-energy-range luminance data, an A/D conversion unit 44b for A/D-converting the high-energy-range luminance data amplified by the amplifier 44a, a correction circuit 44c for performing predetermined correction processing for the luminance data converted by the A/D conversion unit 44b, and an output interface 44d for outputting the luminance data corrected by the correction circuit 44c to the outside as high-energy image data.

The control unit 50 controls detection timings of the transmission X-rays in the low-energy detector 32 and high-energy detector 42 such that the same divisional range $S_n$ in the conveying direction Y of the subject S is detected by both of the detectors 32, 42. The detection timing control by the control unit 50 can reduce deviations in images occurring when the low- and high-energy image data are subjected to subtraction processing.

Since the X-ray irradiator 20 is a point light source from which X-rays spread radially, there are locations where the pixels $32_n$ of the low-energy detector 32 and the pixels $42_n$ of the high-energy detector 42 fail to correspond with each other completely on the upper and lower sides in the Z direction. That is, the correspondence between the respective pixels $32_n$, $42_n$ of the low- and high-energy detectors 32, 42 shifts in the detection direction X more toward ends in the detection direction X. Therefore, the control unit 50 outputs control signals to the correction circuits 34c, 44c and the like such that the respective pixels $32_n$, $42_n$ of the low- and high-energy detectors 32, 42 in the detection direction X of the subject S correspond with each other, thereby regulating the correspondence between the luminance data for each pixel of the low-energy detector 32 and the luminance data for each pixel of the high-energy detector 42.

Specifically, as illustrated in FIG. 3, for example, a calibration member as the subject S is conveyed by the belt conveyor 10 and irradiated with the X-rays from the X-ray irradiator 20. Then, as illustrated in FIG. 3(b), the control unit 50 sets a pixel $32_{100}$ (the 100th pixel from the leftmost end) of the low-energy detector 32 corresponding to one end (depicted left end) of the subject S as a first reference pixel, and a pixel $42_{98}$ (the 98th pixel from the leftmost end) of the high-energy detector 42 corresponding to the one end of the subject S as a second reference pixel. The first and second reference pixels are pixels corresponding with each other and shifted from each other by several pixels in the detection direction X.

The correspondence between the pixels is similarly shifted at the other end (the depicted right side); for example, while a pixel $32_{1100}$ (the 1100th pixel from the leftmost end) of the low-energy detector 32 corresponds to the other end of the subject S, a pixel $42_{1003}$ (the 1003rd pixel from the leftmost end) of the high-energy detector 42 corresponds thereto. Since the corresponding pixels thus shift in the detection direction X, the pixel region corresponding to the subject S covers 1000 pixels from the pixels $32_{100}$ to $32_{1100}$ in the low-energy detector 32 but 1005 pixels from the pixels $42_{98}$ to $42_{1103}$ in the high-energy detector 42. Therefore, the control unit 50 sets the corresponding pixel region of the low-energy detector 32 (1000 pixels of the pixels $32_{100}$ to $32_{1100}$) and the corresponding pixel region of the high-energy detector 42 (1005 pixels of the pixels $42_{98}$ to $42_{1103}$), which differ from each other.

The control unit 50 thus having set the corresponding pixel regions with pixel numbers different from each other performs correction processing such as to increase the number of items of luminance data from the low-energy detector 32 to 100.5% as illustrated in FIG. 4(a), for example, in order for the respective luminance data from the low- and high energy detectors 32, 42 to correspond with each other. The control unit 50 may also perform correction processing such as to decrease the number of items of luminance data from the high-energy detector 42 to 99.5%. An example of processing for correcting (increasing or decreasing) the number of data items is a technique known as so-called linear interpolation, which may be used for changing the number of data items. The example illustrated in FIG. 4(b) connects three actually measured data items A with a virtual line and equally divides the line connecting the actually measured data items so as to yield the number of data items required for interpolation, thereby acquiring 4 corrected data items V, for example.

Figure 5:
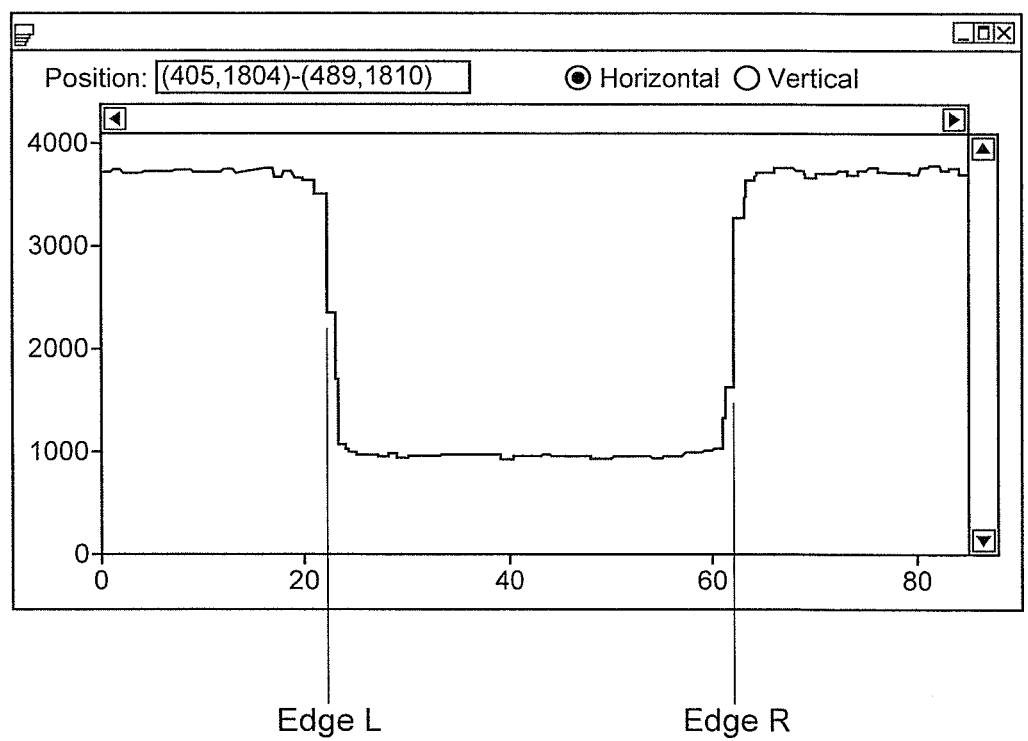
FIG. 5 is a chart illustrating an example of luminance data of X-rays transmitted through a subject to be inspected.

By using such a technique, the control unit 50 corrects the 1000 items of luminance data acquired from the low-energy detector 32, so as to obtain 1005 items of luminance data. The control unit 50 can perform such control as to make thus corrected respective luminance data from the low-energy detector 32 and respective luminance data from the high-energy detectors 42 correspond with each other one by one. Such correction processing is called magnification correction processing; for example, subjecting thus processed both luminance data to predetermined arithmetic processing can yield luminance data corresponding to the subject S as illustrated in FIG. 5. The luminance data in FIG. 5 represents both ends of the subject S as edges L and R, respectively.

The image processor 60 is a device which performs arithmetic processing (subtraction processing) for obtaining difference data between the low-energy image data detected and generated by the low-energy image acquisition unit 30 and the high-energy image data detected and generated by the high-energy image acquisition unit 40, so as to produce a subtraction image which is a synthetic image. For both energy image data inputted to the image processor 60, the control unit 50 controls detection timings such that the image data correspond with each other in the conveying direction Y and regulates the correspondence between the pixels.

The image processor 60 outputs the subtraction image produced by such arithmetic processing to a display or the like so as to render it onto the latter. Displaying the output makes foreign matters and the like included in the subject S visible without destroying the subject S. Data may be outputted alone without displaying the subtraction image, so as to detect foreign matters and the like included in the subject S directly from image data by detection processing thereon.

The analyzer 70 is a device for detecting a positional deviation detail of the X-ray irradiator 20 from a transmittance pattern which is an assembly of ratios of X-ray transmittances of corresponding locations $S_n$ in the subject S detected by the low- and high-energy detectors 32, 42 and performing correction processing corresponding to thus detected positional deviation detail. While the nondestructive inspection device 1 keeps inspecting foreign matters and the like, the focal position of the X-ray irradiator 20 may shift due to thermal expansions and the like, so that the correspondence between the pixels $32_n$, $42_n$ adjusted beforehand by the control unit 50 (e.g., the above-mentioned magnification correction or the like) may be lost, whereby pseudo-edges may occur at the edges L, R (see FIG. 5), which are luminance data corresponding to both ends of the subject S.

In this embodiment, the analyzer 70 detects the positional deviation detail of the X-ray irradiator 20 and performs correction processing for the luminance data, so as to inhibit the pseudo-edges from occurring. As illustrated in FIG. 2, the analyzer 70 has a low-energy transmittance calculation unit 72, a high-energy transmittance calculation unit 74, a detection unit 76, and a correction unit 78.

From the X-ray luminance data detected by the low-energy detector 32, the low-energy transmittance calculation unit 72 calculates the X-ray transmittance of the subject S in the low-energy range for each corresponding region $S_n$. The low-energy transmittance calculation unit 72 includes a correction value calculation unit 72a, a storage unit 72b, a luminance correction unit 72c, and a transmittance calculation unit 72d.

The correction value calculation unit 72a acquires the X-ray luminance data in the low-energy range in a state without the subject S (e.g., a state where the belt conveyor 10 is installed alone) from the low-energy detector 32 at first. Thus acquired X-ray raw luminance data $RL_n$ (n=1 to N, where N is an integer) in the low-energy range is data corresponding to the individual pixels $32_n$ arranged along the detection direction X of the low-energy detector 32 and fluctuates as illustrated in FIG. 6(a), for example.

Figure 6:
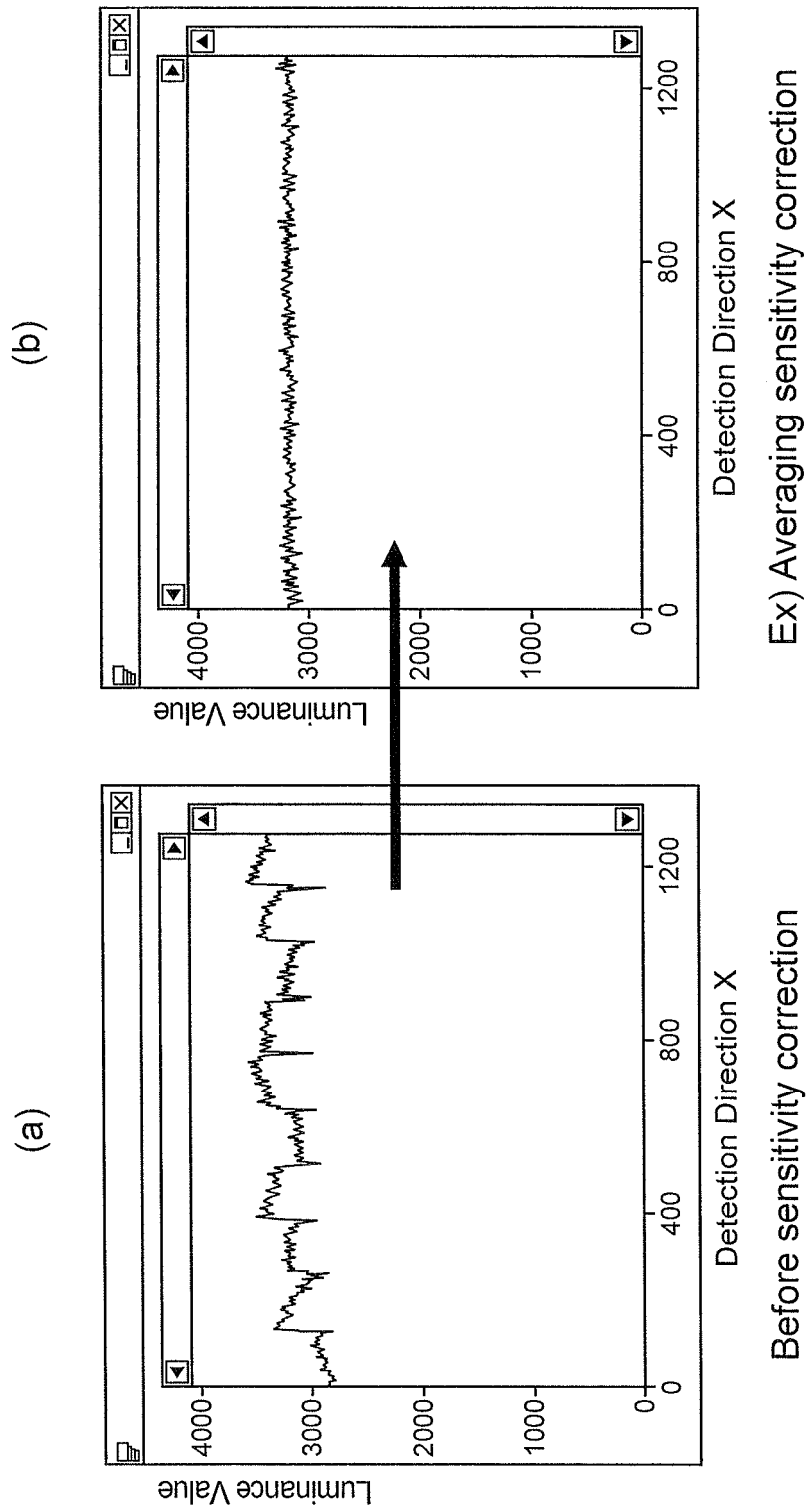
FIGS. 6(a) and 6(b) are charts illustrating outlines of a shading correction, while representing states before and after the correction, respectively.

FIG. 6(a) illustrates an example in which the low-energy detector 32 is constructed by joining 10 line sensors each having 128 pixels in the X direction (i.e., 1280 pixels). Such fluctuations occur even in the state without the subject S because intensity fluctuates along the detection direction X in the X-rays from the X-ray irradiator 20, detection sensitivity fluctuates in the low-energy detector 32, and so forth.

Therefore, by performing shading correction and the like, the correction value calculation unit 72a corrects the luminance fluctuation for each pixel $32_n$ so as to normalize all the raw luminance data $RL_n$ to a luminance value of 3200, for example. Letting DL be thus normalized luminance value and FL be a correction coefficient, their relationship can be represented by the following expression (1):

$$DL = FL \times RL_n \qquad (1)$$

Figure 7:
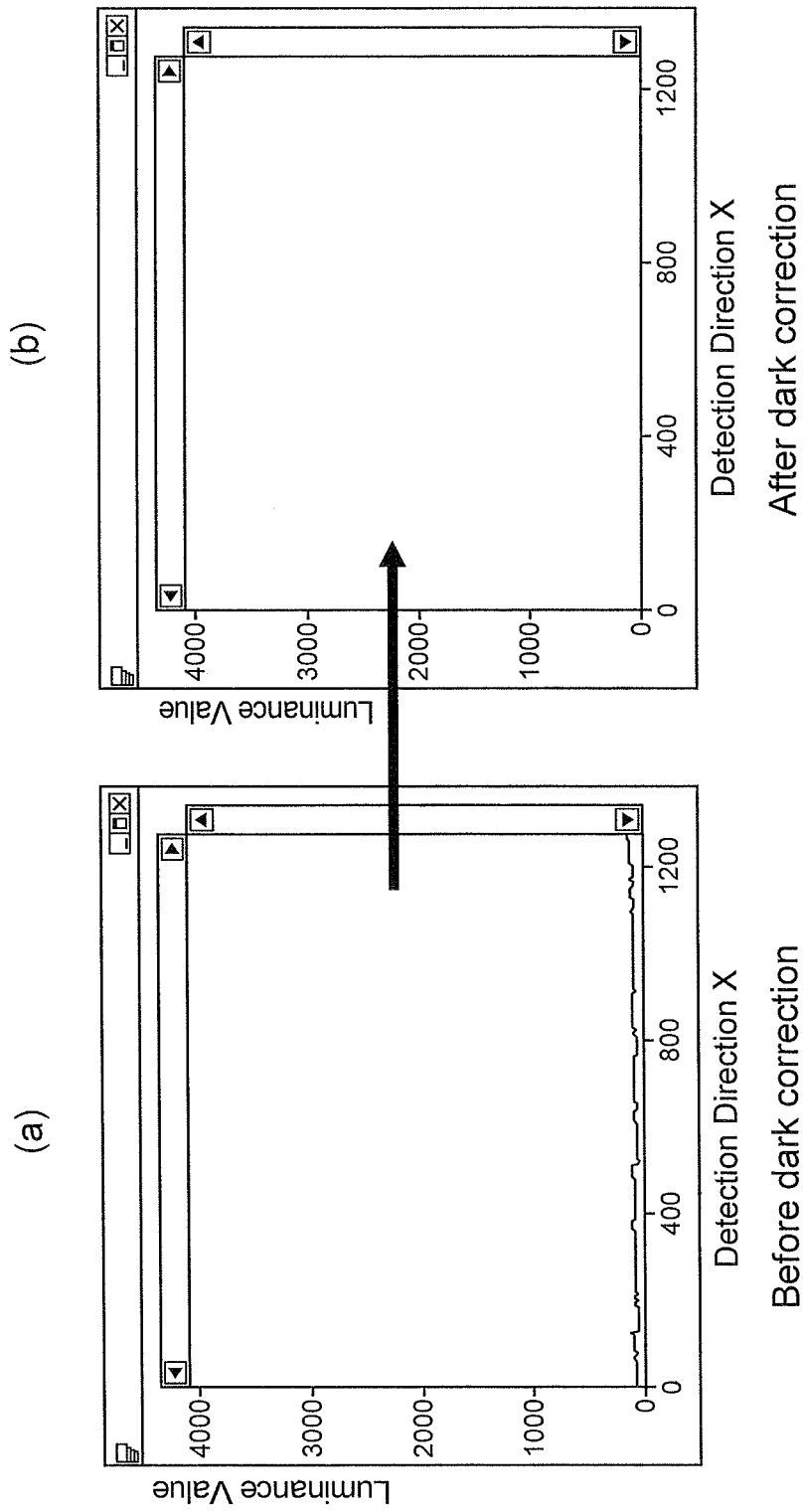
FIGS. 7(a) and 7(b) are charts illustrating outlines of a dark current correction, while representing states before and after the correction, respectively.

Then, from the above expression (1), the correction value calculation unit 72a calculates the correction function FL used in the correction for normalization to the luminance value DL. The correction function FL is a function corresponding to the raw luminance data $RL_n$ from all the pixels $32_n$, and the correction value calculation unit 72a outputs the calculated correction function FL to the storage unit 72b. The correction value calculation unit 72a also outputs the normalized luminance value DL as basic luminance data to the storage unit 72b. The average, maximum, or minimum value of the raw luminance data may be used for the luminance value DL, or the latter may be set as appropriate. As preprocessing for acquiring the X-ray raw luminance data $RL_n$, a dark current correction such as the one illustrated in FIG. 7 may be performed so as to eliminate the initial noise (see FIG. 7(b)), which makes it possible to perform more accurate measurement.

The storage unit 72b stores the correction function FL and the normalized luminance value DL which are outputted from the correction value calculation unit 72a. The storage unit 72b outputs the correction function FL or normalized luminance value DL to the luminance correction unit 72c and transmittance calculation unit 72d, which will be explained later, in response to calls from the luminance correction unit 72c and transmittance calculation unit 72d.

The luminance correction unit 72c acquires X-ray raw luminance $RL_n'$ (n=1 to N, where N is an integer) in the low-energy range in the state where the subject S exists for each corresponding region $S_n$ from the low-energy detector 32. The X-ray raw luminance data $RL_n'$ corresponds to the individual pixels $32_n$ of the low-energy detector 32 and is sequentially acquired for the respective corresponding locations $S_n$ of the subject S.

Upon acquiring the X-ray raw luminance data $RL_n'$ in the low-energy range for each corresponding region $S_n$, the luminance correction unit 72c calls the correction function FL from the storage unit 72b in order to perform a correction similar to the above-mentioned shading correction and multiplies each raw data item by the correction function FL as represented by the following expression (2), so as to obtain corrected individual luminance data $DL_n'$ (n=1 to N, where N is an integer):

$$DL_n' = FL \times RL_n' \qquad (2)$$

Upon acquiring the corrected individual luminance data $DL_n'$, the luminance correction unit 72c outputs the acquired luminance data $DL_n'$ to the transmittance calculation unit 72d.

Upon acquiring the corrected luminance data $DL_n'$, the transmittance calculation unit 72d obtains the normalized luminance value DL from the storage unit 72b and calculates a transmittance $PL = DL_n'/DL$ in the low-energy range. The transmittance calculation unit 72d outputs the calculated transmittance PL to the detection unit 76.

From the X-ray luminance data detected by the high-energy detector 42, the high-energy transmittance calculation unit 74 calculates the X-ray transmittance in the high-energy range of the subject S for each corresponding region $S_n$. Each item of luminance data calculated by the high-energy transmittance calculation unit 74 is data adjusted such as to have the same corresponding region $S_n$ of the subject S as with its corresponding luminance data calculated by the low-energy transmittance calculation unit 72. The high-energy transmittance calculation unit 74 includes a correction value calculation unit 74a, a storage unit 74b, a luminance correction unit 74c, and a transmittance calculation unit 74d.

The correction value calculation unit 74a acquires the X-ray luminance data in the high-energy range in a state without the subject S (e.g., a state where the belt conveyor 10 is installed alone) from the high-energy detector 42 at first. Thus acquired X-ray raw luminance data $RH_n$ (n=1 to N, where N is an integer) in the high-energy range is data corresponding to the individual pixels $42_n$ arranged along the detection direction X of the high-energy detector 42 and fluctuates as with the data from the low-energy detector 32.

Therefore, by performing shading correction and the like, the correction value calculation unit 74a corrects the luminance fluctuation for each pixel $42_n$, so as to normalize all the raw luminance data $RH_n$ to a luminance value of 3200, for example, as with the correction value calculation unit 72a. Letting DH be thus normalized luminance value and FH be a correction coefficient, their relationship can be represented by the following expression (3):

$$DH = FH \times RH_n \qquad (3)$$

Then, from the above expression (3), the correction value calculation unit 74a calculates the correction function FH used in the correction for normalization to the luminance value DH. The correction function FH is a function corresponding to the raw luminance data $RH_n$ from all the pixels $42_n$, and the correction value calculation unit 74a outputs the calculated correction function FH to the storage unit 74b. The correction value calculation unit 74a also outputs the normalized luminance value DH as basic luminance data to the storage unit 74b.

The storage unit 74b stores the correction function FH and the normalized luminance value DH which are outputted from the correction value calculation unit 74a. The storage unit 74b outputs the correction function FH or normalized luminance value DH to the luminance correction unit 74c and transmittance calculation unit 74d, which will be explained later, in response to calls from the luminance correction unit 74c and transmittance calculation unit 74d.

The luminance correction unit 74c continuously acquires X-ray raw luminance $RH_n'$ (n=1 to N, where N is an integer) in the high-energy range in the state where the subject S exists for each corresponding region $S_n$ from the high-energy detector 42. The X-ray raw luminance data $RH_n'$ corresponds to the individual pixels $42_n$ of the high-energy detector 42 and is sequentially acquired for the respective corresponding locations $S_n$ of the subject S.

Upon acquiring the X-ray raw luminance data $RH_n'$ in the high-energy range for each corresponding region $S_n$, the luminance correction unit 74c calls the correction function FH from the storage unit 74b in order to perform a correction similar to the above-mentioned shading correction and multiplies each raw data item by the correction function FH as represented by the following expression (4), so as to acquire corrected individual luminance data $DH_n'$ (n=1 to N, where N is an integer):

$$DH_n' = FH \times RH_n' \qquad (4)$$

Upon acquiring the corrected individual luminance data $DH_n'$, the luminance correction unit 74c outputs the acquired luminance data $DH_n'$ to the transmittance calculation unit 74d.

Upon acquiring the corrected luminance data $DH_n'$, the transmittance calculation unit 74d obtains the normalized luminance value DH from the storage unit 74b and calculates a transmittance $PH = DH_n'/DH$ in the high-energy range. The transmittance calculation unit 74d outputs the calculated transmittance PH to the detection unit 76.

By computing a ratio between the transmittance PL ($=DL_n'/DL$) calculated by the low-energy transmittance calculation unit 72 and the transmittance PH ($=DH_n'/DH$) calculated by the high-energy transmittance calculation unit 74, the detection unit 76 detects the positional deviation detail of the X-ray irradiator 20. This ratio is represented by the following expression (5):

$$\text{Transmittance ratio} = PH/PL \qquad (5)$$

The detection unit 76 determines whether or not a transmittance pattern as a data series for each region $S_n$ of the transmittance ratio PH/PL based on the above-mentioned expression (5) matches any of patterns illustrated in FIGS. 8(a) to 8(d). That is, the detection unit 76 determines whether there is a place where the transmittance ratio PH/PL is smaller than a threshold A (lower threshold) or greater than a threshold B (upper threshold).

Though specific relationships between the individual patterns represented in FIG. 8 and the positional deviation detail of the X-ray irradiator 20 will be explained later. The pattern represented in FIG. 8(a) illustrates a case where the X-ray irradiator 20 is shifted to one side (left side) of the detection direction X. The pattern represented in FIG. 8(b) illustrates a case where the X-ray irradiator 20 is shifted to the other side (right side) of the detection direction X. The pattern represented in FIG. 8(c) illustrates a case where the X-ray irradiator 20 is shifted to the lower side of the irradiation direction Z. The pattern represented in FIG. 8(d) illustrates a case where the X-ray irradiator 20 is shifted to the upper side of the irradiation direction Z.

This embodiment sets the threshold A to 1, for which a reason will be explained in brief. Since X-rays having higher energy are easier to pass through objects, if X-rays having traveled the same route (i.e., the same material part) in the subject S are detected in low- and high-energy ranges, the transmittance in the high-energy range will always be higher. For example, when X-rays transmitted through a wire are detected in low- and high-energy ranges, the transmittance in the low-energy range is 0.181, while the transmittance in the high-energy range is 0.327, whereby the transmittance ratio PH/PL=1.807, which is greater than 1.

That is, when the transmittance ratio PH/PL is greater than 1, X-rays having traveled the same route (i.e., the same material part) in the subject S are highly likely to be detected in the low- and high-energy ranges, whereby it can be determined that the correspondence adjusted beforehand such that the pixels $32_n$ of the low-energy detector 32 and the pixels $42_n$ of the high-energy detector 42 correspond with each other is maintained. When the transmittance in the high-energy range is lower than the transmittance in the low-energy range, on the other hand, X-rays having failed to travel the same route (having passed different material parts) in the subject S are highly likely to be compared with each other, whereby it can be determined that the correspondence adjusted beforehand such that the pixels $32_n$ of the low-energy detector 32 and the pixels $42_n$ of the high-energy detector 42 correspond with each other is not maintained.

This embodiment uses a test piece made of aluminum as a calibration member. According to the transmittance of X-rays through aluminum, the transmittance ratio PH/PL at the time when the aluminum test piece is irradiated with the X-rays falls within the range of 1.1 to 2, for example. Therefore, in addition to the lower threshold A, this embodiment sets the upper threshold B to 2. The upper threshold B is changed for each member to be irradiated with the X-rays, so as to be adjusted into a range suitable for the member. The upper threshold B preferably varies its value depending on the X-ray transmittance in the material of the subject S to be irradiated with the X-rays and is set appropriately according to the X-ray transmittance of the subject S.

The relationship between the individual patterns represented in FIGS. 8(a) to 8(d) and the positional deviation detail of the X-ray irradiator 20 will now be explained more specifically with reference to FIGS. 9 to 14.

Figure 9:
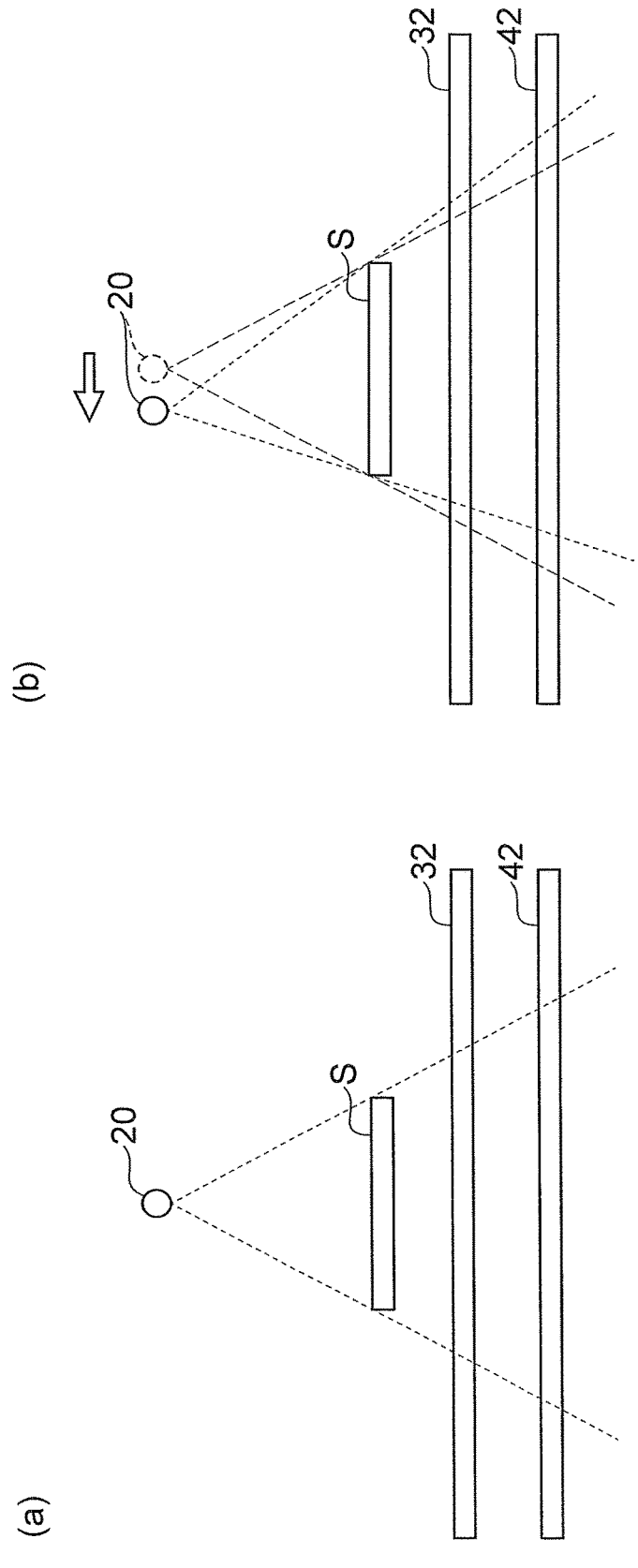
FIGS. 9(a) and 9(b) are diagrams illustrating a case where an X-ray source is shifted to one side of a detection direction X in the nondestructive inspection device depicted in FIG. 1, while representing states before and after the shift, respectively.
Figure 10:
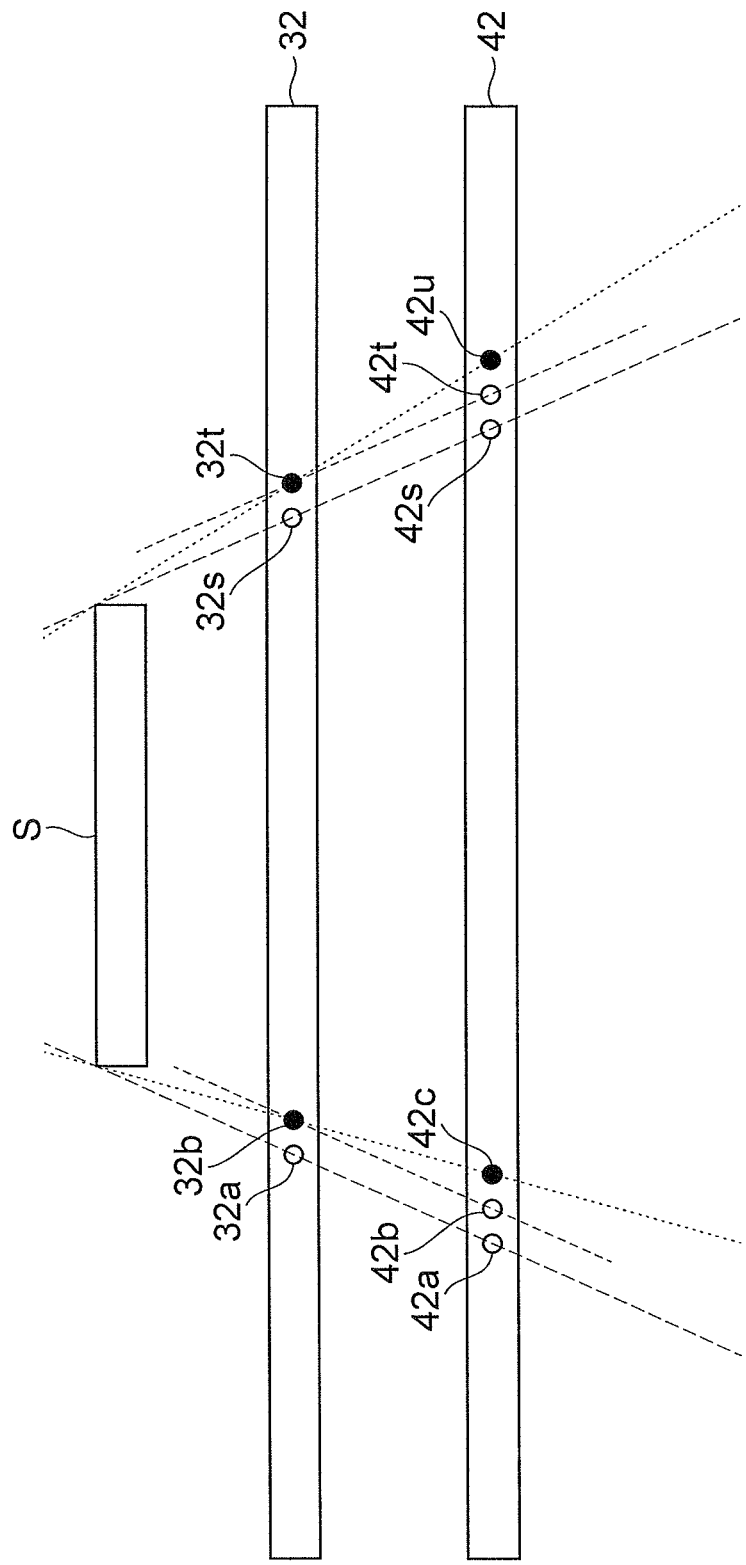
FIG. 10 is a diagram enlarging a part of FIG. 9(b).

First, the case where the X-ray irradiator 20 is shifted to one side (depicted left side) of the detection direction X will be explained with reference to FIGS. 9 and 10. When the X-ray irradiator 20 shifts from the position illustrated in FIG. 9(a) to that illustrated in FIG. 9(b), pixels of the detectors 32, 42 detecting both ends of the subject S and thereabout also shift individually. Specifically, before the X-ray irradiator 20 shifts, a pixel 32a of the detector 32 and a pixel 42a of the detector 42 correspond with each other at a location corresponding to the left end of the subject S, while a pixel 32s of the detector 32 and a pixel 42s of the detector 42 correspond with each other at a location corresponding to the right end of the subject S.

When the X-ray irradiator 20 shifts to the left side of the detection direction X, however, a pixel 32b of the detector 32 and a pixel 42c of the detector 42 correspond with each other at a location corresponding to the left end of the subject S, while a pixel 32t of the detector 32 and a pixel 42u of the detector 42 correspond with each other at a location corresponding to the right end of the subject S. Meanwhile, in the detectors 32, 42, the magnification correction and the like are performed by the control unit 50 as mentioned above so that the pixels correspond with each other, whereby a pixel 42b is allocated as the pixel of the detector 42 corresponding to the pixel 32b of the detector 32, while a pixel 42t is allocated as the pixel of the detector 42 corresponding to the pixel 32t of the detector 32.

The pixel 32b of the detector 32 detects the subject S, whereas the pixel 42b of the detector 42 corresponding to the pixel 32b detects a state where the subject S does not exist (air). As a result, for example, the transmittance PL from the pixel 32b detecting the subject S is 33%, while the transmittance PH from the pixel 42b not detecting the subject S is substantially 100%, whereby their transmittance ratio PH/PL is 3.03. That is, the location corresponding to one end of the subject S yields a value greater than the upper threshold B.

The pixel 32t of the detector 32 detects the state where the subject S does not exist (air), whereas the pixel 42t of the detector 42 corresponding to the pixel 32t detects the subject S. As a result, for example, the transmittance PL from the pixel 32t not detecting the subject S is substantially 100%, while the transmittance PH from the pixel 42t detecting the subject S is 33%, whereby their transmittance ratio PH/PL is 0.33. That is, the location corresponding to the other end of the subject S yields a value smaller than the lower threshold A.

Thus, when the X-ray irradiator 20 shifts to the left side of the detection direction X, such a transmittance pattern as that illustrated in FIG. 8(a) appears so as to become higher than the upper threshold B at the location corresponding to the left end of the subject S and lower than the lower threshold A at the location corresponding to the right end of the subject S. When the X-ray irradiator 20 shifts to the right side of the detection direction X, by contrast, such a transmission pattern as that illustrated in FIG. 8(b), which is symmetrical to that of FIG. 8(a) about a line, appears so as to become higher than the upper threshold B at the location corresponding to the right end of the subject S and lower than the lower threshold A at the location corresponding to the left end of the subject S.

Figure 12:
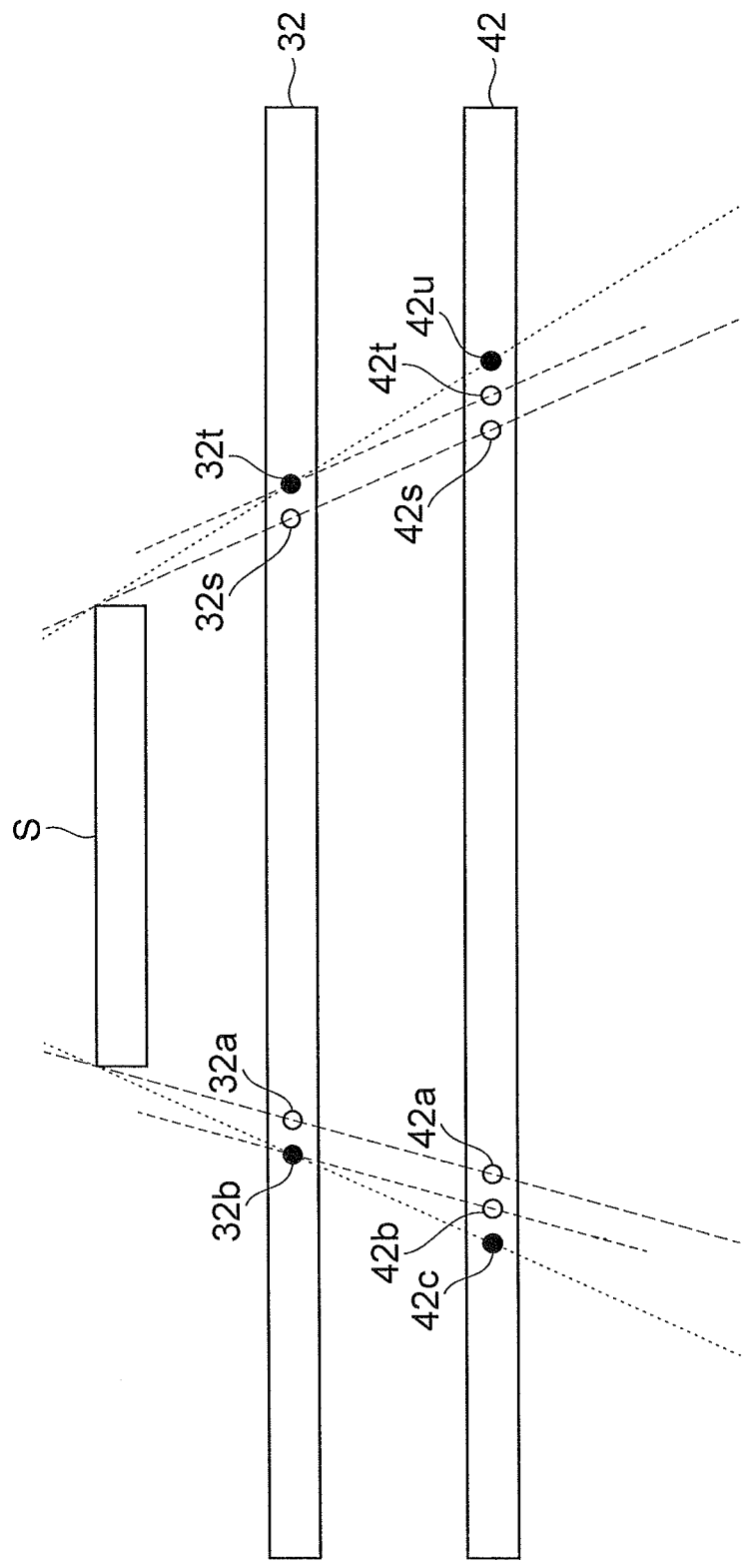
FIG. 12 is an enlarged view of a part of FIG. 11(b).

The case where the X-ray irradiator 20 shifts to the lower side of the irradiation direction Z will now be explained with reference to FIGS. 11 and 12. When the X-ray irradiator 20 shifts from the position illustrated in FIG. 11(a) to the position illustrated in FIG. 11(b), the pixels of the detectors 32, 42 detecting both ends of the subject S and thereabout when irradiated by the X-ray irradiator 20 also shift individually. Specifically, before the X-ray irradiator 20 shifts, the pixel 32a of the detector 32 and the pixel 42a of the detector 42 correspond with each other at a location corresponding to the left end of the subject S, while the pixel 32s of the detector 32 and the pixel 42s of the detector 42 correspond with each other at a location corresponding to the right end of the subject S.

When the X-ray irradiator 20 shifts to the lower side of the irradiation direction Z, however, the pixel 32b of the detector 32 and the pixel 42c of the detector 42 correspond with each other at a location corresponding to the left end of the subject S, while a pixel 32t of the detector 32 and the pixel 42u of the detector 42 correspond with each other at a location corresponding to the right end of the subject S. Meanwhile, in the detectors 32, 42, the magnification correction and the like are performed by the control unit 50 as mentioned above so that the pixels correspond with each other, whereby the pixel 42b is allocated as the pixel of the detector 42 corresponding to the pixel 32b of the detector 32, while the pixel 42t is allocated as the pixel of the detector 42 corresponding to the pixel 32t of the detector 32.

The pixel 32b of the detector 32 detects the state where the subject S does not exist (air), whereas the pixel 42b of the detector 42 corresponding to the pixel 32b detects the subject S. As a result, for example, the transmittance PL from the pixel 32b not detecting the subject S is substantially 100%, while the transmittance PH from the pixel 42b detecting the subject S is 33%, whereby their transmittance ratio PH/PL is 0.33. That is, the location corresponding to one end of the subject S yields a value smaller than the lower threshold A.

The pixel 32t of the detector 32 detects the state where the subject S does not exist (air), whereas the pixel 42t of the detector 42 corresponding to the pixel 32t detects the subject S. As a result, for example, the transmittance PL from the pixel 32t not detecting the subject S is substantially 100%, while the transmittance PH from the pixel 42t detecting the subject S is 33%, whereby their transmittance ratio PH/PL is 0.33. That is, the location corresponding to the other end of the subject S also yields a value smaller than the lower threshold A. Thus, when the X-ray irradiator 20 shifts to the lower side of the irradiation direction Z, such a transmittance pattern as that illustrated in FIG. 8(c) appears so as to become smaller than the lower threshold A at the locations corresponding to both of the left and right ends of the subject S.

Figure 13:
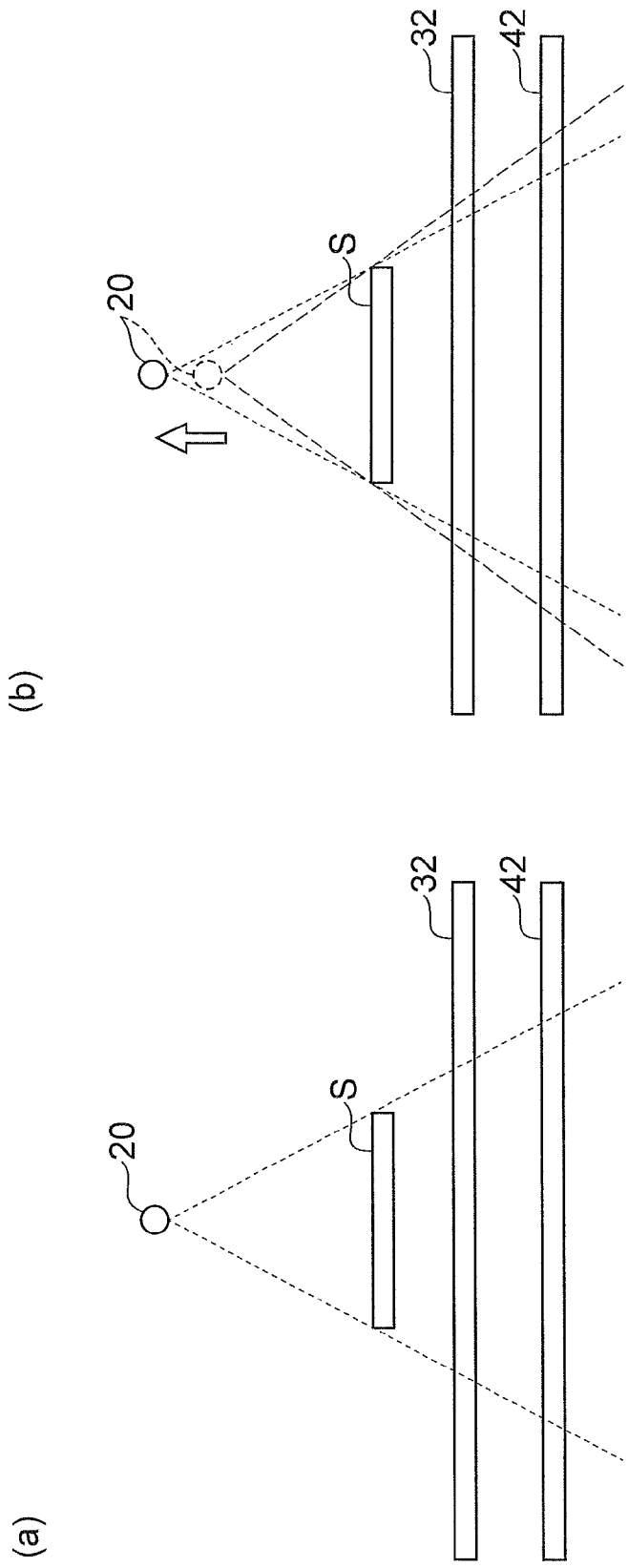
FIGS. 13(a) and 13(b) are diagrams illustrating a case where the X-ray source is shifted to the upper side of the irradiation direction Z in the nondestructive inspection device depicted in FIG. 1, while representing states before and after the shift, respectively.
Figure 14:
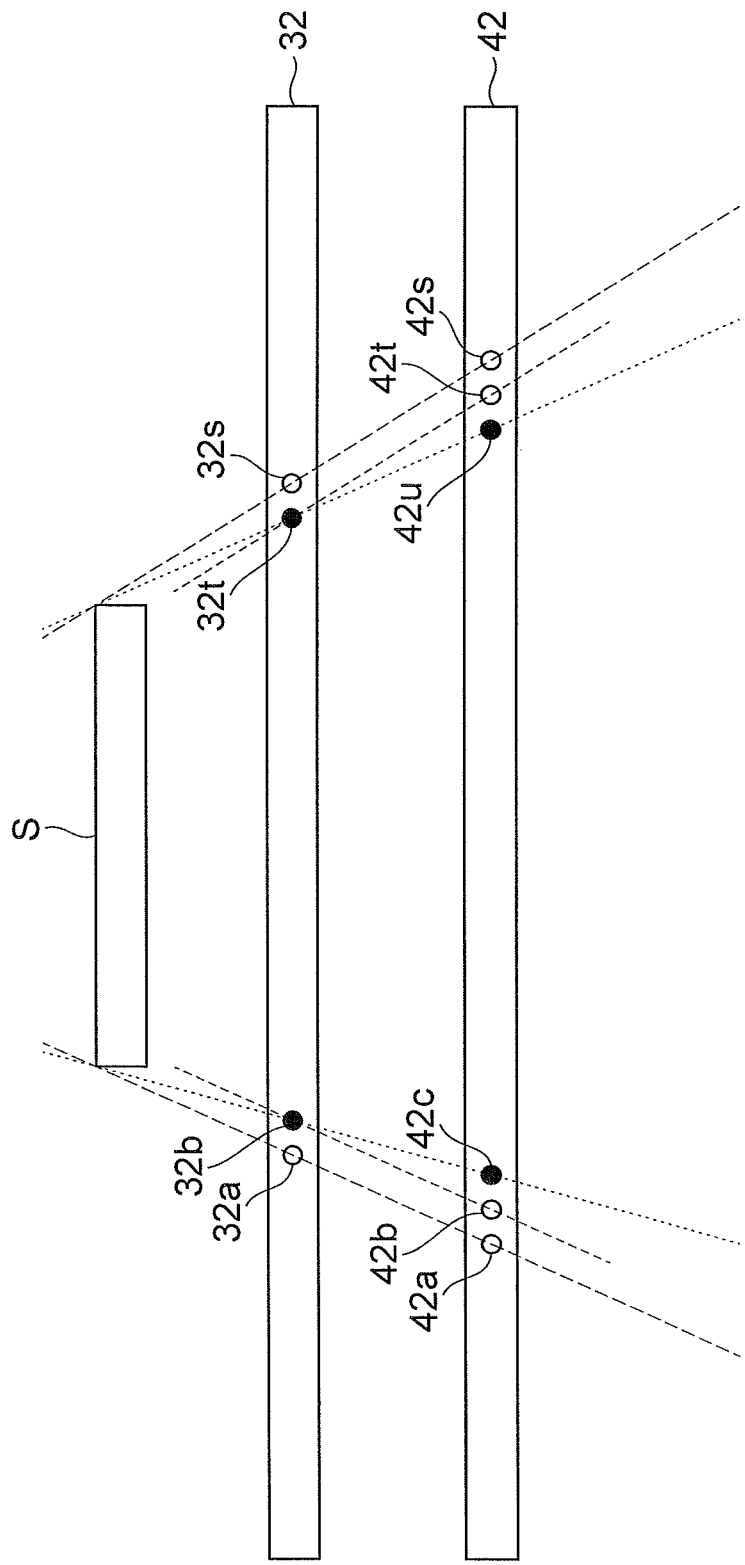
FIG. 14 is a diagram enlarging a part of FIG. 13(b).

The case where the X-ray irradiator 20 shifts to the upper side of the irradiation direction Z will now be explained with reference to FIGS. 13 and 14. When the X-ray irradiator 20 shifts from the position illustrated in FIG. 13(a) to the position illustrated in FIG. 13(b), the pixels of the detectors 32, 42 detecting both ends of the subject S and thereabout when irradiated by the X-ray irradiator 20 also shift individually. Specifically, before the X-ray irradiator 20 shifts, the pixel 32a of the detector 32 and the pixel 42a of the detector 42 correspond with each other at a location corresponding to the left end of the subject S, while the pixel 32s of the detector 32 and the pixel 42s of the detector 42 correspond with each other at a location corresponding to the right end of the subject S.

When the X-ray irradiator 20 shifts to the upper side of the irradiation direction Z, however, the pixel 32b of the detector 32 and the pixel 42c of the detector 42 correspond with each other at a location corresponding to the left end of the subject S, while the pixel 32t of the detector 32 and the pixel 42u of the detector 42 correspond with each other at a location corresponding to the right end of the subject S. Meanwhile, in the detectors 32, 42, the magnification correction and the like are performed by the control unit 50 as mentioned above so that the pixels correspond with each other, whereby the pixel 42b is allocated as the pixel of the detector 42 corresponding to the pixel 32b of the detector 32, while the pixel 42t is allocated as the pixel of the detector 42 corresponding to the pixel 32t of the detector 32.

The pixel 32b of the detector 32 detects the subject S, whereas the pixel 42b of the detector 42 corresponding to the pixel 32b detects the state where the subject S does not exist (air). As a result, for example, the transmittance PL from the pixel 32b detecting the subject S is 33%, while the transmittance PH from the pixel 42b not detecting the subject S is substantially 100%, whereby their transmittance ratio PH/PL is 3.03. That is, the location corresponding to one end of the subject S yields a value greater than the upper threshold B.

The pixel 32t of the detector 32 detects the subject S, whereas the pixel 42t of the detector 42 corresponding to the pixel 32t detects the state where the subject S does not exist (air). As a result, for example, the transmittance PL from the pixel 32t detecting the subject S is 33%, while the transmittance PH from the pixel 42t not detecting the subject S is substantially 100%, whereby their transmittance ratio PH/PL is 3.03. That is, the location corresponding to the other end of the subject S also yields a value greater than the upper threshold B. Thus, when the X-ray irradiator 20 shifts to the upper side of the irradiation direction Z, such a transmittance pattern as that illustrated in FIG. 8(d) appears so as to become greater than the upper threshold B at the locations corresponding to both of the left and right ends of the subject S.

The detection unit 76 produces a detection result indicating whether the transmittance pattern constituted by an assembly of the acquired transmittance ratio PH/PL corresponds to any of the patterns of FIG. 8 or falls between the thresholds A, B without matching to any of the patterns and outputs the result to the correction unit 78.

Upon receiving the detection result concerning the positional deviation detail of the X-ray irradiator 20 from the detection unit 76, the correction unit 78 generates according to the positional deviation detail a correction instruction signal for correcting at least one of X-ray luminance data detected by the low- and high-energy detectors 32, 42.

An example of signals generated by the correction unit 78 is such an instruction signal that, when it is determined by the detection unit 76 that the X-ray irradiator 20 is shifted in the detection direction X, one reference pixel 42a in the reference pixels 32a, 42a for making the luminance data from the detectors 32, 42 correspond with each other is moved in increments of one pixel to the side opposite from the side of the detection direction X to which the X-ray irradiator 20 is shifted.

The correction signal may also be one in which the other reference pixel 32a is moved to the same side of the detection direction X as with the X-ray irradiator 20 in increments of one pixel or by a sub-pixel unit such as 0.1 pixel.

The correction signal may include a correction instruction for performing readjustment processing for readjusting the magnification of each of the pixels constituting both of the detectors 32, 42 along with thus resetting the reference pixel.

Another example of correction indication signals generated by the correction unit 78 is such a signal that, when it is determined by the detection unit 76 that the X-ray irradiator 20 is shifted in the irradiation direction Z, readjustment processing for readjusting the magnification of each of the pixels constituting the detectors 32, 42 is performed. This signal may enhance and reduce the magnification of the pixels of the low-energy detector 32 when the X-ray irradiator 20 shifts to the lower and upper sides of the irradiation direction Z, respectively.

When the X-ray irradiator 20 shifts to the lower side of the irradiation direction Z before thus readjusting the magnification, the correction signal may be such that one reference pixel 42a in the reference pixels 32a, 42a for making the luminance data from the detectors 32, 42 correspond with each other is moved outward in increments of one pixel or such that the other reference pixel 32a is moved inward in increments of one pixel. When the X-ray irradiator 20 shifts to the upper side of the irradiation direction Z, on the other hand, the correction signal may be such that one reference pixel 42a in the reference pixels 32a, 42a for making the luminance data from the detectors 32, 42 correspond with each other is moved inward in increments of one pixel or such that the other reference pixel 32a is moved outward in increments of one pixel.

The correction unit 78 outputs such a correction signal to the control unit 50 and causes the control unit 50 and the correction circuits 34c, 44c and the like controlled by the control unit 50 to execute processing such as resetting of the reference pixels or readjustment of the magnification, thereby correcting the luminance data from the detectors 32, 42.

Meanwhile, the above-mentioned embodiment performs correction processing such that the luminance value DL used in the low-energy transmittance calculation unit 72 and the luminance value DH used in the high-energy transmittance calculation unit 74 become the same value. In this case, the calculated transmittances have the same denominator, which makes it unnecessary to calculate the transmittances directly, whereby the transmittance calculation units 72, 74 may be constructed without the transmittance calculation units 72d, 74d. In this structure, the luminance correction unit 72c outputs the luminance data $DL_n'$ as it is to the detection unit 76, while the luminance correction unit 74c outputs the luminance data $DH_n'$ as it is to the detection unit 76. Here, the corrected luminance data $DL_n'$ functions as one of values indicating the transmittance in the low-energy range, while the corrected luminance data $DH_n'$ functions as one of values indicating the transmittance in the high-energy range.

In the above-mentioned case, upon acquiring the corrected luminance data $DL_n'$ and $DH_n'$ from the luminance correction units 72c and 74c, respectively, the detector 76 calculates the transmittance ratio=PH/PL from these luminance data. Since the luminance values DL and DH are the same, the transmittance ratio PH/PL is represented by the following expression (7):

$$\text{Transmittance ratio} = PH/PL = DH_n'/DL_n' \quad (7)$$

Then, the detection unit 76 performs detection processing similar to the processing mentioned above, so as to detect the positional deviation detail of the X-ray irradiator 20.

Figure 15:
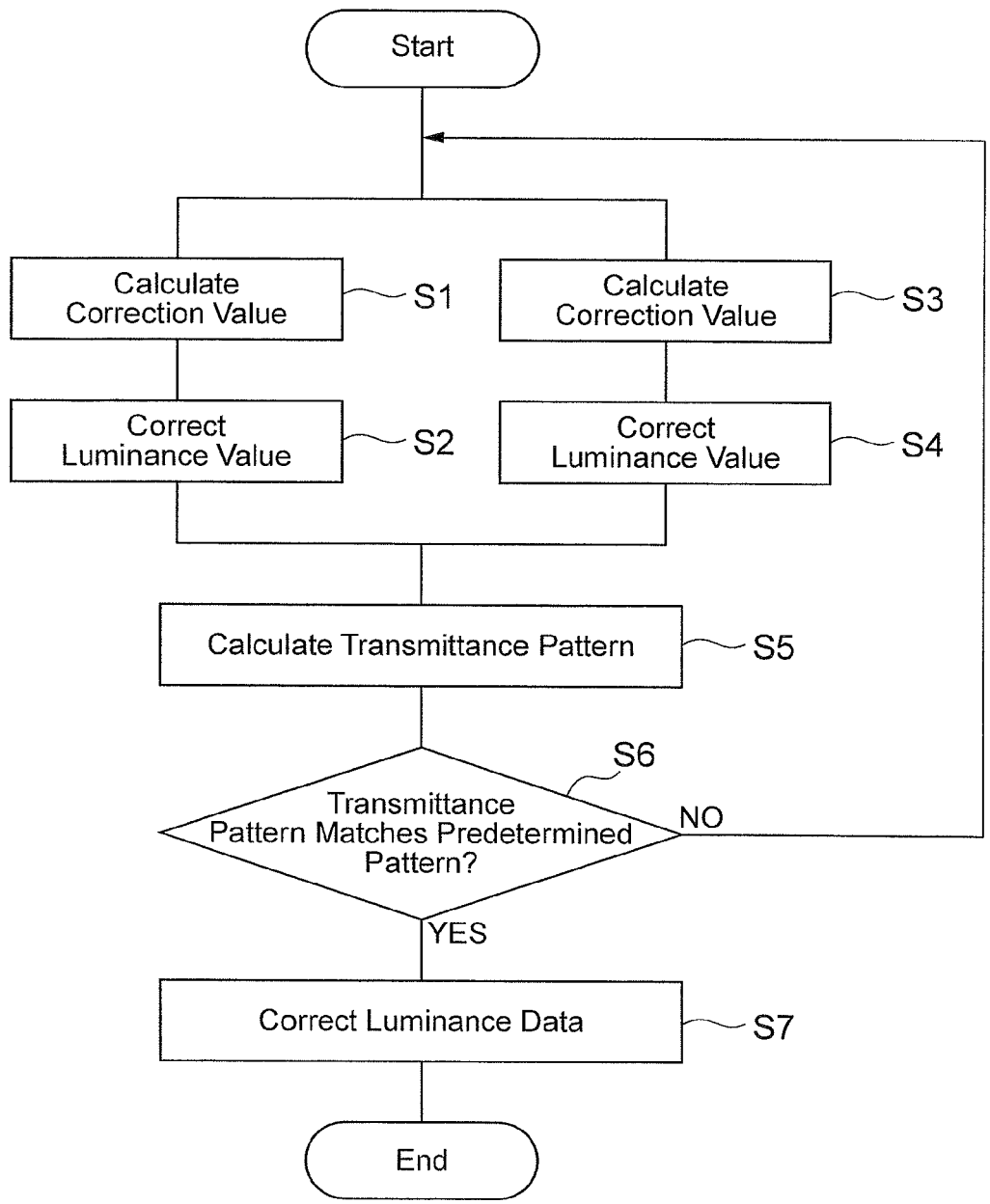
FIG. 15 is a flowchart illustrating a correction method in the nondestructive inspection device depicted in FIG. 1.

A correction method for detecting the positional deviation detail of the X-ray irradiator 20 and correcting the luminance data in the nondestructive inspection device 1 will now be explained with reference to FIG. 15. In the following explanation, the corrected luminance data $DL_n'$ and $DH_n'$ are utilized as they are as the transmittances PL and PH, respectively.

First, from the low-energy detector 32, the correction value calculation unit 72a acquires the X-ray luminance data $RL_n$ in the low-energy range in the state without the subject S. Thereafter, the correction value calculation unit 72a subjects the X-ray luminance data $RL_n$ to shading correction and the like, so as to correct fluctuations in luminance among the pixels $32_n$, thereby normalizing all the raw luminance data $RL_n$ to a luminance value of 3200, for example. Then, from the above-mentioned expression (1), the correction value calculation unit 72a calculates the correction function FL used in the correction for normalization to the luminance value DL (step S1).

Subsequently, from the low-energy detector 32, the luminance correction unit 72c acquires the X-ray raw luminance data $RL_n'$ in the low energy range in the state where the subject S exists. Upon acquiring the X-ray raw luminance data $RL_n'$ in the low-energy range, the luminance correction unit 72c calls the correction function FL from the storage unit 72b and multiplies each raw data item by the correction function FL as represented by the above-mentioned expression (2), so as to obtain corrected individual luminance data $DL_n'$ (step S2). The corrected individual luminance data $DL_n'$ thus obtained is outputted to the detection unit 76.

From the high-energy detector 42, the correction value calculation unit 74a acquires the X-ray luminance data $RH_n$ in the high-energy range in the state without the subject S. Thereafter, the correction value calculation unit 74a subjects the X-ray luminance data $RH_n$ to shading correction and the like, so as to correct fluctuations in luminance among the pixels $42_n$, thereby normalizing all the raw luminance data $RH_n$ to a luminance value of 3200, for example. Then, from the above-mentioned expression (3), the correction value calculation unit 74a calculates the correction function FH used in the correction for normalization to the luminance value DH (step S3).

Subsequently, from the high-energy detector 42, the luminance correction unit 74c acquires the X-ray raw luminance data $RH_n'$ in the high energy range in the state where the subject S exists. Upon acquiring the X-ray raw luminance data $RH_n'$ in the high-energy range, the luminance correction unit 74c calls the correction function FH from the storage unit 74b and multiplies each raw data item by the correction function FH as represented by the above-mentioned expression (4), so as to obtain corrected individual luminance data $DH_n'$ (step S4). The corrected individual luminance data $DH_n'$ thus obtained is outputted to the detection unit 76.

Next, from the transmittance PL ($=DL_n'$) calculated by the low-energy transmittance calculation unit 72 and the transmittance PH ($=DH_n'$) calculated by the high-energy transmittance calculation unit 74, the detection unit 76 computes a transmittance pattern as a data series for each region $S_n$ of the transmittance ratio PH/PL (step S5). Then, the detection unit 76 determines whether the computed transmittance pattern matches any of patterns illustrated in FIGS. 8(a) to 8(d) or, matches none of the patterns illustrated in FIGS. 8(a) to 8(d).

When the transmittance pattern matches any of the patterns of FIGS. 8(a) to 8(d) according to the determination at step S6, the method proceeds to step S7, where the luminance data is corrected in conformity to the matched pattern as mentioned above. An example of luminance data correction is such that, when it is determined by the detection unit 76 that the X-ray irradiator 20 is shifted in the detection direction X, one reference pixel 42a in the reference pixels 32a, 42a for making the luminance data from the detectors 32, 42 correspond with each other is moved in increments of one pixel to the side opposite from the side of the detection direction X to which the X-ray irradiator 20 is shifted. Along with thus resetting the reference pixel, readjustment processing for readjusting the magnification of each of the pixels constituting both of the detectors 32, 42 may be performed.

When the transmittance pattern matches none of the patterns of FIGS. 8(a) to 8(d) according to the determination at step S6, by contrast, the method returns to steps S1, S3, so as to repeat similar processing.

In the nondestructive inspection device 1, the foregoing can detect early if pixels of the detectors 32, 42 stacked in two stages fail to correspond with each other and correct luminance data such that the pixels $32_n$, $42_n$ correspond with each other again.

Thus, the nondestructive inspection device 1 of this embodiment calculates values indicating respective transmittances in both energy ranges of X-rays transmitted through the subject S from the luminance data and detects the positional deviation detail of the X-ray irradiator 20 according to the ratio between the values indicating the transmittances. While radiations such as X-rays have such a property as to be easier to pass through an object as their energy is higher, referring to the ratio of the values indicating the transmittances of the object in both detectors adjusted such that their pixels and the like correspond with each other can detect if and how the pixels of the detectors 32, 42 fail to correspond with each other, whereby the positional deviation detail of the X-ray irradiator 20 can be seen. As a result, the nondestructive inspection device 1 can detect early if the pixels of the detectors 32, 42 stacked in two stages fail to correspond with each other and correct the luminance data from the detectors 32, 42 such that the pixels can correspond with each other again.

In addition, the nondestructive inspection device 1 calculates the values indicating the transmittances in both energy ranges of X-rays by utilizing luminance data. This makes it easy to determine the transmittances without requiring new detectors to be provided separately.

In the nondestructive inspection device 1 and correction method, the detection unit 76 stores therein two thresholds A, B of upper and lower limits set by the X-ray transmittance of the subject S and detects the positional deviation detail of the X-ray irradiator 20 by comparing the ratio between the values indicating both transmittances with the thresholds A, B. In this case, for detecting the positional deviation detail of the X-ray irradiator 20, the thresholds are set according to a distinct radiation transmittance for each subject S to be inspected, whereby the positional deviation detail of the X-ray irradiator 20 can be seen more securely.

In the nondestructive inspection device 1 and correction method, each of the detectors 32, 42 has a detection region extending in a detection direction intersecting the conveying and irradiation directions, while the detection unit 76 detects the positional deviation detail of the radiation source by comparing with the upper and lower thresholds A, B a transmittance pattern constituted by an assembly of ratios between the values indicating both transmittances while corresponding to the detection region. Therefore, the positional deviation detail of the radiation source can be detected by comparing the transmittance pattern with the thresholds, whereby the detection processing can be performed simpler.

While preferred embodiments of the present invention are explained in detail in the foregoing, the present invention is not limited thereto but can be modified in various ways. For example, while the analysis unit 70 determines the positional deviation of the X-ray irradiator 20 by comparing the transmittance ratio PH/PL with the thresholds A, B in the above-mentioned embodiments, a difference between the transmittance PL in the low-energy range and the transmittance PH in the high-energy range may be compared with the thresholds A, B as represented by the following expression (8), so as to detect the positional deviation detail of the X-ray irradiator 20.

$$\text{Threshold } B > PH-PL > \text{Threshold } A \tag{8}$$

In this case, for example, a location where the transmittance pattern constituted by the assembly of PH−PL is smaller than 0 which is the threshold A and a location where PH−PL is greater than the threshold B are detected, and according thereto the correction unit 78 performs predetermined correction processing. The threshold B in this case can also be set as appropriate according to the X-ray transmittance of the subject S. The same holds when a transmittance ratio PL/PH which is the inverse of the transmittance ratio PH/PL is employed as a reference in place thereof.

The correction functions FL, FH, which are set such that the basic luminance data DL and DH are identical to each other in the above-mentioned embodiments, may be set such that the basic luminance data DL and DH do not become the same value depending on the luminance data acquired. In this case, however, the transmittances cannot omit their denominators and thus are required to be compared with each other. The detection by comparison is similar to that in the above-mentioned embodiments.

While the above-mentioned embodiments employ X-ray luminance data in the ranges in the state without the subject S (e.g., a state where the belt conveyor 10 is installed alone) as the basic luminance data for calculating the transmittances PH, PL, when inspecting the subject S contained in a tray mounted on the belt conveyor 10 separate therefrom, X-ray luminance data may be determined in a state including the tray in addition to the belt conveyor 10, i.e., in a part not included in the subject S, as the basic luminance data for calculating the transmittances PH, PL, and the transmittances may be calculated by using them.

The correspondence between the detectors 32, 42, which is compared for each of the pixels $32_n$, $42_n$ in the above-mentioned embodiments, may be compared for each predetermined region, and reference pixels, magnification, and the like may be set with reference thereto. This can prevent errors caused by noise and the like from being detected. While the above-mentioned embodiments set the reference pixels $32_{100}$ and $42_{98}$ with reference to left edges corresponding to the left ends of the detectors 32, 42, the reference edges may be set with reference to right edges corresponding to the right ends of the detectors 32, 42 or a center point as a matter of course.

While the above-mentioned embodiments are explained by a case where the image correction units 34, 44 and the transmittance calculation units 72, 74 are provided separately, the transmittances may be calculated in the transmittance calculation units 72, 74 by using data outputted from output interfaces of the image correction units 34, 44. That is, functions of the transmittance calculation units 72, 74 may be partly or wholly in common with the image correction units 34, 44.

REFERENCE SIGNS LIST

1 . . . Nondestructive inspection device; 10 . . . Belt conveyor; 20 . . . X-ray irradiator; 32 . . . Low-energy detector; 42 . . . High-energy detector; 50 . . . Control unit; 70 . . . Analyzer; 72 . . . Low-energy transmittance calculation unit; 74 . . . High-energy transmittance calculation unit; 76 . . . Detection unit; 78 . . . Correction unit.

The invention claimed is:

1. A nondestructive inspection device comprising:
   a conveyor unit that conveys a subject to be inspected in a predetermined direction;
   an X-ray radiation source that irradiates the conveyor unit with a radiation directed so as to intersect a conveying direction caused by the conveyor unit;
   a first X-ray radiation detector that detects the radiation emitted from the radiation source in a first energy range;
   a second X-ray radiation detector that detects the radiation emitted from the radiation source in a second energy range higher than the first energy range;
   a first calculation unit that calculates from luminance data of the radiation detected by the first radiation detector a value indicating a first transmittance in the first energy range of the radiation transmitted from the radiation source through the subject;
   a second calculation unit that calculates from luminance data of the radiation detected by the second radiation detector a value indicating a second transmittance in the second energy range of the radiation transmitted from the radiation source through the subject;
   a detection unit that detects a positional deviation detail of the radiation source according to a ratio or difference between the value indicating the first transmittance calculated by the first calculation unit and the value indicating the second transmittance calculated by the second calculation unit; and
   a correction unit that corrects, when the positional deviation detail of the radiation source is detected by the detection unit, according to the positional deviation detail at least one of the luminance data of the radiation detected by the first and second radiation detectors.

2. The nondestructive inspection device according to claim 1,
   wherein the detection unit stores therein two thresholds of upper and lower limits set by a radiation transmittance of the subject and detects the positional deviation detail of the radiation source by comparing the ratio or difference between the values indicating the first and second transmittances with both of the upper and lower thresholds.

3. The nondestructive inspection device according to claim 2,
   wherein each of the first and second radiation detectors has a detection region extending in a detection direction intersecting the conveying and irradiation directions; and wherein the detection unit detects the positional deviation detail of the radiation source by comparing with the upper and lower thresholds a transmittance pattern constituted by an assembly of ratios or differences of values indicating the first and second transmittances while corresponding to the detection region.

4. The nondestructive inspection device according to claim 3,
wherein the detection unit determines that the radiation source is shifted in the detection direction when a location corresponding to one end of the subject in the transmittance pattern is higher than the upper threshold while a location corresponding to the other end of the subject in the transmittance pattern is lower than the lower threshold.

5. The nondestructive inspection device according to claim 4,
wherein, when it is determined by the detection unit that the radiation source is shifted in the detection direction, the correction unit performs reset processing for setting a new reference pixel by moving at least one of reference pixels for causing respective luminance data from the first and second radiation detectors to correspond with each other to another pixel, so as to correct at least one of the luminance data from the first and second radiation detectors.

6. The nondestructive inspection device according to claim 4,
wherein, when it is determined by the detection unit that the radiation source is shifted in the detection direction, the correction unit performs readjustment processing for readjusting a magnification of each of pixels constituting the first and second radiation detectors, so as to correct one of the luminance data from the first and second radiation detectors.

7. The nondestructive inspection device according to claim 3,
wherein the detection unit determines that the radiation source is shifted in the irradiation direction if each of locations corresponding to both ends of the subject in the transmittance pattern is lower than the lower threshold or higher than the upper threshold.

8. The nondestructive inspection device according to claim 7,
wherein, when it is determined by the detection unit that the radiation source is shifted in the irradiation direction, the correction unit performs readjustment processing for readjusting a magnification of each of pixels constituting the first and second radiation detectors, so as to correct one of the luminance data from the first and second radiation detectors.

9. The nondestructive inspection device according to claim 7,
wherein, when it is determined by the detection unit that the radiation source is shifted in the irradiation direction, the correction unit performs reset processing for setting a new reference pixel by moving at least one of reference pixels for causing respective luminance data from the first and second radiation detectors to correspond with each other to another pixel, so as to correct at least one of the luminance data from the first and second radiation detectors.

10. The nondestructive inspection device according to claim 1,
wherein the second radiation detector is located downstream of the first radiation detector in the irradiation direction of the radiation.

11. A correction method, in a nondestructive inspection device comprising a conveyor unit that conveys a subject to be inspected in a predetermined direction, an X-ray radiation source that irradiates the conveyor unit with a radiation directed so as to intersect a conveying direction caused by the conveyor unit, a first X-ray radiation detector that detects the radiation emitted from the radiation source in a first energy range, and a second X-ray radiation detector that detects the radiation emitted from the radiation source in a second energy range higher than the first energy range, for correcting at least one of luminance data detected by the first and second radiation detectors, the method comprising:
a first calculation step of calculating from luminance data of the radiation detected by the first radiation detector a value indicating a first transmittance in the first energy range of the radiation transmitted from the radiation source through the subject;
a second calculation step of calculating from luminance data of the radiation detected by the second radiation detector a value indicating a second transmittance in the second energy range of the radiation transmitted from the radiation source through the subject;
a detection step of detecting a positional deviation detail of the radiation source according to a ratio or difference between the value indicating the first transmittance calculated at the first calculation step and the value indicating the second transmittance calculated at the second calculation step; and
a correction step of correcting, when the positional deviation detail of the radiation source is detected at the detection step, according to the positional deviation detail at least one of the luminance data of the radiation detected by the first and second radiation detectors.

* * * * *